(12) United States Patent
Hossain et al.

(10) Patent No.: US 12,158,427 B2
(45) Date of Patent: *Dec. 3, 2024

(54) SERS ELECTRODE HAVING TRANSITION METAL OXIDE NANOPARTICLE LAYER

(71) Applicant: KING FAHD UNIVERSITY OF PETROLEUM AND MINERALS, Dhahran (SA)

(72) Inventors: Mohammad Kamal Hossain, Dhahran (SA); Qasem Ahmed Drmosh, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/738,109

(22) Filed: Jun. 10, 2024

(65) Prior Publication Data

US 2024/0328954 A1 Oct. 3, 2024

Related U.S. Application Data

(63) Continuation of application No. 17/894,271, filed on Aug. 24, 2022, now Pat. No. 12,031,918.

(51) Int. Cl.
  *G01N 21/65* (2006.01)
  *B82Y 30/00* (2011.01)
  (Continued)

(52) U.S. Cl.
  CPC .......... *G01N 21/658* (2013.01); *B82Y 30/00* (2013.01); *C23C 14/185* (2013.01); *C23C 14/5806* (2013.01); *G01N 33/5438* (2013.01)

(58) Field of Classification Search
  CPC .. G01N 21/658; G01N 33/5438; B82Y 30/00; C23C 14/185; C23C 14/5806
  (Continued)

(56) References Cited

U.S. PATENT DOCUMENTS

| 9,745,645 B2 | 8/2017 | Drmosh et al. |
| 2007/0138459 A1* | 6/2007 | Wong ................... C01G 25/006 977/811 |
| 2010/0129623 A1 | 5/2010 | Johansson et al. |

FOREIGN PATENT DOCUMENTS

| CN | 103695984 B | 5/2016 |
| CN | 108950493 A | 12/2018 |
| CN | 109612976 B | 11/2021 |

OTHER PUBLICATIONS

Mohammad Kamal Hossain, et al., "Silver Nanoparticles and Nanorings for Surface-Enhanced Raman Scattering", Plasmonics, vol. 17, Jan. 27, 2022, pp. 1051-1064 (Abstract only).

(Continued)

*Primary Examiner* — Md M Rahman
(74) *Attorney, Agent, or Firm* — Oblon, McClelland, Maier & Neustadt, L.L.P.

(57) ABSTRACT

A surface-enhanced Raman scattering (SERS)-active electrode include a solid support; a porous oxide layer containing transition metal oxide nanoparticles present on a surface of the solid support and has a mean pore size of 2 to 30 nm; and at least one of noble metal nanoneedles and noble metal nanorings present on the porous oxide layer. The noble metal nanoneedles have an average length of 350-800 nm, a flat end with an average width in a range of 100-150 nm, and a pointed end. The noble metal nanorings have a thickness of 50-300 nm and are present in the form of annular clusters having various elliptical shapes with an average diameter in a range of 35-60 nm.

6 Claims, 30 Drawing Sheets

(51) Int. Cl.
*C23C 14/18* (2006.01)
*C23C 14/58* (2006.01)
*G01N 33/543* (2006.01)

(58) Field of Classification Search
USPC .......................................................... 356/301
See application file for complete search history.

(56) References Cited

OTHER PUBLICATIONS

Dusik Bae, et al., "Hierarchically Well-Ordered Array of Concentric Silver Nanorings for Highly Sensitive Surface-Enhanced Raman Scattering Substrate", The Journal of Physical Chemistry C, vol. 116, Issue 50, Nov. 26, 2012, pp. 26523-26528 (Abstract only).

\* cited by examiner

SERS ELECTRODE HAVING TRANSITION METAL OXIDE NANOPARTICLE LAYER

CROSS-REFERENCE TO RELATED APPLICATIONS

The present application is a Continuation of U.S. application Ser. No. 17/894,271, now allowed, having a filing date of Aug. 24, 2022.

BACKGROUND

Technical Field

The present disclosure is directed to Raman spectroscopy and spectroscopic imaging and, more particularly relates to a surface-enhanced Raman scattering-active electrode, a method of making the surface-enhanced Raman scattering-active electrode, and a method of detecting an analyte using the surface-enhanced Raman scattering-active electrode.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Surface-enhanced Raman scattering (SERS) is known as a powerful label free analytical tool. SERS, being a subset of standard Raman spectroscopic techniques, provides detailed and fingerprint information about materials at the molecular level. The SERS technique significantly enhances the Raman signal from analyte molecules. Two main mechanisms are typically considered to be responsible for the surface enhancement; electromagnetic (EM) mechanism (EM enhancement) and chemical mechanism (CE enhancement). Typically, the EM mechanism is the dominant contributor to the enhancement, reaching enhancement factors as high as $10^5$-$10^7$. In the EM mechanism, a surface plasmon resonance of a suitable plasmonic material creates a much stronger electromagnetic field located very close to the plasmonic material, typically within a few to tens of nanometers. This enhanced electromagnetic field is referred to as the localized surface plasmon resonance (LSPR)-mediated electromagnetic (EM) field and is the main component that makes such tremendous amplification of standard Raman signal of target analyte. However, such EM field localizations are heavily influenced by the nanometric morphology of the plasmonic material and substrate, as well as the characteristics of the excitation used, in SERS measurements. Therefore, this is a key challenge to fabricate a cost-effective plasmonic substrates that facilitate higher enhancement and provide reproducible and predictable SERS-activity for a wide range of analytes.

SERS-active substrates comprising plasmonic materials are mainly fabricated using two different techniques: physical deposition and wet-chemical synthesis. However, both techniques have several limitations. For example, in wet-chemical synthesis, synthesized colloidal nanoparticles have surfactants or other surface ligands that inhibit target analyte to be at the point of maximal EM field enhancement (the "hot spot") at the time of measuring. Also, lack of control in nanomorphology and nanoassembly makes it difficult to fabricate reproducible and predefined SERS-active substrate. Physical deposition techniques such as lithography, template method, and thermal vapor deposition are expensive and labor-intensive. For example, in thermal deposition technique, an adequate control over deposition time, power, and a strict environment condition to develop the SERS-active substrate is required. Further such SERS substrates developed via both techniques typically include a distribution of hot sites only in X-Y plane (i.e Z=0) that reduces the chances of the target analyte to be at the hot sites.

Most studies related to SERS hotspots (SHSs) relate to the fabrication of plasmonic nanostructures that induce strong EM near-field.

Although 0D- or 1D-plasmonic nanoparticles, such as isolated nanoparticles or nanorods suspended in a homogeneous medium exhibits moderate SERS enhancement, 0D and 1D nanoparticles facilitates the strong and wider distribution of EM near-field. Self-assembly of uniform and regular shape nanoparticles such as nanospheres, nanocubes, nanobars, nanostars, nanoprisms and mesocages exhibits much more intense SERS activity.

Silver and gold (Au) nanoparticles as efficient SERS-active substrates have been reported with a high enhancement factor [Hossain, M. K. (2020). Nanoassembly of Au nanoparticles: An active substrate for size-dependent surface-enhanced Raman scattering. Spectrochimica Acta Part A: Molecular and Biomolecular Spectroscopy, 242, 118759]. Ag nanobars were activated with higher SERS enhancement at near-infrared (NIR) excitation [Zhang, Q., et al. (2012). Synthesis of Ag nanobars in the presence of single-crystal seeds and a bromide compound, and their surface-enhanced Raman scattering (SERS) properties. Langmuir, 28 (24), 9047-9054]. Size-controlled Ag nanodecahedrons were reported to be an active SERS substrate with the capability to target analyte of thiol, disulfide, isothiocyanate or benzotriazole groups [Lu, H., et al. (2013). Synthesis of size-controlled silver nanodecahedrons and their application for core-shell surface enhanced Raman scattering (SERS) tags. Rsc Advances, 3 (3), 966-974]. Ag octahedral mesocages exhibited high reproducibility and an unusual SERS enhancement in the order of 8 to 9 [Fang, J., et al. (2011). Polyhedral silver mesocages for single particle surface-enhanced Raman scattering-based biosensor. Biomaterials, 32 (21), 4877-4884]. Homogenously distributed multiple effective hot spots on the surface of a single mesoparticle were demonstrated to be the reason for a high SERS enhancement factor.

Moskovits and his coworkers elaborated theoretically a different paradigm of LSPRs coupling through dipole-dipole interaction model. The second generation of SHSs is coupling of localized EM near-field, amplifying the SERS signal further, and improving the SERS enhancement. A well-ordered and self-assembled monolayer of Au nanoparticles were reported as an efficient SERS-active substrate with enhancement factor as high as 8 to 10 orders [Hossain, M. K. (2020). Nanoassembly of Au nanoparticles: An active substrate for size-dependent surface-enhanced Raman scattering. Spectrochimica Acta Part A: Molecular and Biomolecular Spectroscopy, 242, 118759; Hossain, M. K., et al. (2015). Anisotropic Au nanoassembly: a study on polarization-dependent and polarization-selective surface-enhanced Raman scattering. Physical Chemistry Chemical Physics, 17 (6), 4268-4276; Hossain, M. K., et al. (2013). Tunable SERS using Au nanoaggregates on an elastomeric substrate. Nanoscale, 5 (19), 8945-8950; Hossain, M. K., et al. (2009). Surface-enhanced Raman scattering: realization of localized surface plasmon resonance using unique substrates and methods. Analytical and bioanalytical chemistry, 394 (7), 1747-1760; Hossain, M. K., et al. (2017). Interstitial-dependent enhanced photoluminescence: a near-field microscopy on single spheroid to dimer, tetramer, and few particles Au nanoassembly. The Journal of Physical Chemistry C, 121 (4), 2344-2354; Hossain, M. K., et al. (2015). A topography-metrology correlation in nanoscale probed by near-field scanning optical microscopy. Plasmonics, 10 (2), 447-454]. The main factor for such high SERS enhancement was due to plasmon coupling at different interstitials across the nanoassembly. Self-assembled Au nanorods have been reported as efficient SERS-active substrates [Velleman, L., et al. (2017). Monitoring plasmon coupling and SERS enhancement through in situ nanoparticle spacing modulation. Faraday discussions, 205, 67-83]. The high SERS enhancement was elucidated based on the plasmon peak shift as well as plasmon couplings. On the other hand, vertical Au nanorods exhibited strong enhancement in the SERS study [Dong, J., et al. (2019). Nanoscale vertical arrays of Au nanorods by self-assembly: physical mechanism and application. Nanoscale research letters, 14 (1), 1-9]. The target analyte as low as $10^{-11}$ M concentration was detected by such Au nanorods and the plausible mechanism was related to strong plasmon coupling. However, these nanostructures, particularly self-assembled nanoparticulates, facilitate SHSs distribution across 2D regions (i.e. x-y direction), whereas three-dimensional (3D) nanostructures support additional sites of SHSs along the z-axis. Therefore, analytes get more opportunity to adsorb at or around the strong EM near-field and thus SERS enhancement becomes higher. 3D SHSs-distributed SERS-active substrate using Ag clusters led nanoring structures and plasmonic pollen grain like nanostructures [Hossain, M. K., et al. (2021). Plasmonic Pollen Grain Nanostructures: A Three-Dimensional Surface-Enhanced Raman Scattering (SERS)-Active Substrate. Chemistry—An Asian Journal, 16 (13), 1807-1819; Hossain, M. K., et al. (2021). Half-Raspberry-Like Bimetallic Nanoassembly: Interstitials Dependent Correlated Surface Plasmon Resonances and Surface-Enhanced Raman Spectroscopy. Physical Chemistry Chemical Physics; Hossain, M. K., et al. (2021). Clusters-based silver nanorings: An active substrate for surface-enhanced Raman scattering. Spectrochimica Acta Part A: Molecular and Biomolecular Spectroscopy, 263, 120141]. The substrate showed strong SERS enhancement, although the coverage densities of such nanostructures were reported to be low with reference in its entirety to standard SERS-active substrates. Au decorated Ag nanocone and Ag mists decorated Au nanoassembly were reported that 3D distribution of SHSs caused strong SERS enhancement [Hossain, M. K., et al. (2015). A topography-metrology correlation in nanoscale probed by near-field scanning optical microscopy. Plasmonics, 10 (2), 447-454; Zuo, Z., et al. (2021). Multiple plasmon couplings in 3D hybrid Au-nanoparticles-decorated Ag nanocone arrays boosting highly sensitive surface enhanced Raman scattering. Nano Research, 1-9; Seo, S., et al. (2018). 3D plasmon coupling assisted sers on nanoparticle-nanocup array hybrids. Scientific reports, 8 (1), 1-11]. A hybrid system consisting of nanoparticles-nanocup array confirming the further distribution of 3D plasmon coupling led to higher SERS enhancement [Seo, S., et al. (2018). 3D plasmon coupling assisted sers on nanoparticle-nanocup array hybrids. Scientific reports, 8 (1), 1-11]. SERS-active substrates consisting of 0D, 1D and 2D nanoparticles facilitate the population of SHSs and affect reproducible and enhanced SERS-activities.

Accordingly it is one object of the present disclosure to provide a surface-enhanced Raman scattering-active electrode, a method of making the surface-enhanced Raman scattering-active electrode, and a method of detecting an analyte using the surface-enhanced Raman scattering-active electrode.

SUMMARY

In an exemplary embodiment, the present disclosure relates to a surface-enhanced Raman scattering (SERS)-active electrode. The SERS active electrode includes a solid support; a porous oxide layer comprising transition metal oxide nanoparticles present on a surface of the solid support and has a mean pore size of 2 to 30 nm; and at least one of noble metal nanoneedles and noble metal nanorings present on the porous oxide layer. The noble metal nanoneedles have an average length of 350-800 nm, a flat end with an average width in a range of 100-150 nm, and a pointed end. The noble metal nanorings have a thickness of 50-300 nm and are present in the form of annular clusters having various elliptical shapes with an average diameter in a range of 35-60 nm.

In some embodiments, the noble metal is selected from the group consisting of gold, platinum, palladium, ruthenium, rhodium, osmium, silver, copper, mercury, rhenium, iridium, and alloys thereof.

In some embodiments, the solid support is glass, the noble metal is silver, and the transition metal oxide nanoparticles are wurtzite zinc oxide nanoparticles which are crystalline by PXRD and have a mean particle size of 10 to 50 nm.

In some embodiments, zinc oxide nanoparticles are present in the porous oxide layer as agglomerates having a mean size of 150 to 300 nm, and a coverage density of the noble metal nanoneedles present on the porous oxide layer is $4 \times 10^8 - 6 \times 10^8$ particles/cm$^{-2}$.

In some embodiments, a coverage density of the noble metal nanorings present on the zinc oxide is $7 \times 10^3 - 9 \times 10^3$ particles/cm$^{-2}$ and the noble metal nanorings are present as annular clusters of 6-10 nanorings.

In some embodiments, 1.2-8 times greater enhancement in a surface-enhanced Raman scattering activity is obtained when the surface-enhanced Raman scattering-active electrode comprises the noble metal nanorings in comparison to the noble metal nanoneedles.

According to another aspect, the present disclosure relates to a method of making the surface-enhanced Raman scattering-active electrode. The method includes depositing the porous oxide layer onto the solid support to form a first oxide-coated support; depositing a layer of the noble metal onto the first oxide-coated support to form a second-coated support; and annealing the second-coated support at 400 to 800° C. to form the surface-enhanced Raman scattering-active electrode.

In some embodiments, depositing the porous oxide layer is performed by direct current sputtering at a plasma power of 50 to 200 W for 10 to 60 minutes in oxygen gas and the transition metal to solid support distance is fixed at 5 to 20 cm.

In some embodiments, the layer of noble metal is sputtered at a plasma power of 5 to 20 W for 1 to 20 second in argon gas, and a base pressure and a working pressure of the sputtering is maintained at $1 \times 10^{-6}$ to $10 \times 10^{-6}$ torr.

In some embodiments, the method comprises annealing the second-coated support in argon gas at 500 to 700° C. for 1 to 3 hours with a ramp of a heating rate of 10 to 30° C./min to form noble metal nanoneedles on the porous oxide layer.

In some embodiments, the method comprises annealing the second-coated support in nitrogen gas at 600 to 800° C.

for 1 to 3 hours with a ramp of a heating rate of 10 to 30° C./min to form noble metal nanorings on the porous oxide layer.

In some embodiments, annealing the second-coated support is performed in inert atmosphere.

In some embodiments, the porous oxide layer comprises transition metal oxide nanoparticles having a mean particle size of 10 to 50 nm, and wherein the transition metal oxide nanoparticles are present in the porous oxide layer as agglomerates having a mean size of 150 to 300 nm.

The present disclosure also relates to a method of obtaining a Raman spectrum of an analyte. The method includes depositing the analyte onto the surface-enhanced Raman scattering electrode of claim 1 to form a sample; exposing the sample to laser light such that a portion of the laser light is scattered by the sample to form scattered light; and detecting the scattered light.

In some embodiments, the analyte contacts at least one selected from the group consisting of the porous oxide layer, the noble metal nanoneedles, and the noble metal nanorings, and wherein the laser light has a wavelength of 522 to 542 nm and the noble metal nanorings have an enhancement factor of greater than $1.1 \times 10^6$ to $5.9 \times 10^6$.

In some embodiments, the analyte includes at least one biological molecule selected from the group consisting of a protein, a deoxyribonucleic acid sequence, a ribonucleic acid sequence, an amino acid, a peptide, a nucleotide, a nucleoside, and a neurotransmitter.

In some embodiments, the analyte includes at least one synthetic molecule.

In some embodiments, the analyte includes Rhodamine 6G.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2B (i)-(iv): Zoom-in view of four typical Ag NNs-ZnO confirming the variation in lengths and bases along with further details of the Ag NNs-ZnO.

DETAILED DESCRIPTION

Figure 1A:
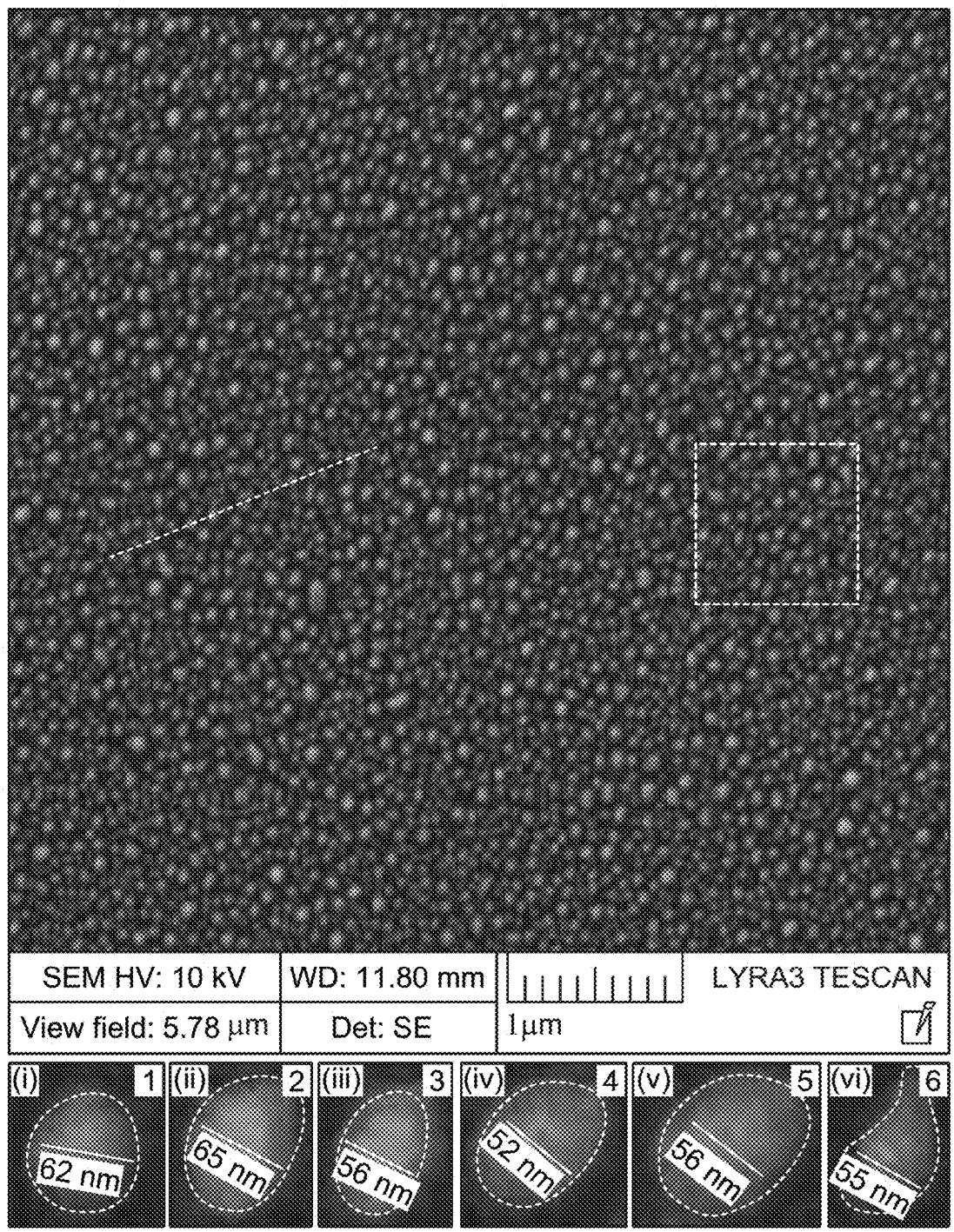
FIG. 1A illustrates High-resolution FESEM micrograph of Ag NPs-ZnO, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

According to one aspect, the present disclosure relates to a surface-enhanced Raman scattering (SERS)-active electrode (hereinafter interchangeably referred to as SERS active electrode). The SERS active electrode includes a solid support. A porous oxide layer comprising transition metal oxide nanoparticles present on a surface of the solid support and has a mean pore size of 2 to 30 nm, and at least one of noble metal nanoneedles and noble metal nanorings present on the porous oxide layer. The solid support may be any suitable material known to one of ordinary skill in the art. Examples of the solid support include silicon wafer, glass, thermoplastic, metal oxide such as ITO, transparent, opaque, porous, non-porous and any inert material that does not react with the porous oxide layer. In addition, examples of suitable solid support include, but are not limited to glass, sapphire, diamond, silicon, geranium, a binary semiconductor such as gallium arsenide, zinc sulfide, and cadmium selenide, a metal such as titanium, nickel, chromium, aluminum, and copper, and mixtures thereof.

The solid support may be cleaned prior to use in the method. Such cleaning may involve cleansing with a suitable solvent, for example ethanol, acetone, deionized water, or mixtures thereof. The cleaning may take place at room temperature. The cleaning may involve ultrasonication. The glass solid support used herein may have anti-reflective and self-cleaning properties. The glass may be any suitable type of glass, for example soda lime glass, borosilicate glass, aluminosilicate glass, lead glass, annealed glass, tempered glass, chemically strengthened glass, laminated glass, quartz, fluorine-doped tin oxide (FTO), indium tin oxide (ITO), and fused silica.

The use of certain polymers, such as polyether ether ketone (PEEK), polytetrafluroethylene, polyvinylidene difluoride, polycarbonate, poly(methyl methacrylate), and the like may be suitable in certain embodiments. However, such polymers are not typically compatible with the temperatures used in the method of forming the surface-enhanced Raman scattering-active electrode described below. In some embodiments in which the solid support is such a polymer, the polymer may be incorporated after the preparation of the surface-enhanced Raman scattering-active electrode.

The noble metal nanoneedles have an average length of 100-1200 nm, preferably 200-1000 nm, preferably 300-900 nm, preferably 350-800 nm, a flat end with an average width in a range of 20-300 nm, preferably 50-250 nm, preferably 100-200 nm, preferably 100-150 nm, and a pointed end.

The noble metal nanorings have a thickness of 10-500 nm, preferably 20-400 nm, preferably 50-300 nm and are present in the form of annular clusters having various elliptical shapes with an average diameter in a range of 10-100 nm, preferably 15-90 nm, preferably 20-80 nm, preferably 30-70 nm, preferably 35-60 nm.

In some embodiments, the noble metal is selected from the group consisting of gold, platinum, palladium, ruthenium, rhodium, osmium, silver, copper, mercury, rhenium, iridium, and alloys thereof. Examples of copper alloys include, but are not limited to gilding metal; Muntz metal; beryllium copper; nickel silver; cupronickel; Dunce metal; bronzes such as manganese bronze, tin bronze, leaded tin bronze, aluminum bronze, silicon bronze, phosphor bronze, commercial bronze, architectural bronze, mild bronze, bell metal, arsenical bronze, speculum metal, and cymbal alloy; and brasses such as Abyssinian gold, admiralty brass, Aich's alloy, aluminum brass, arsenical brass, cartridge brass, common brass, DZR brass, delta metal, free machining brass, high brass, leaded brass, low brass, manganese brass, naval brass, nickel brass, Nordic gold, drichalcum, Prince's metal, red brass (also known as gunmetal), tombac, silicon tombac, tonval brass, and yellow brass. Other exemplary alloys include gold alloys with copper and silver (colored gold, crown gold, electrum), gold alloys with rhodium (rhodite), gold alloys with copper (rose gold, tumbaga), gold alloys with nickel and palladium (white gold), gold alloys including the addition of platinum, manganese, aluminum, iron, indium and other appropriate elements or mixtures thereof, silver alloys with copper (shibuichi, sterling silver, Tibetan silver, Britannia silver), silver alloys with copper and gold (goloid), silver alloys with copper and germanium (argentium sterling silver), silver alloys with platinum (platinum sterling), silver alloys with copper (silver graphite), silver alloys including the addition of palladium, zinc, iridium, and tin and other appropriate elements or mixtures thereof, platinum alloys with gold, platinum alloys with cobalt, platinum alloys with rare earth elements, and platinum alloys with nickel.

In an embodiment, the solid support is glass.

In an embodiment, the noble metal is silver.

In an embodiment, the transition metal oxide nanoparticles are wurtzite zinc oxide nanoparticles which are crystalline by PXRD and have a mean particle size of 5 to 100 nm, preferably 5 to 90 nm, preferably 5 to 80 nm, preferably 5 to 70 nm, preferably 5 to 60 nm, preferably 5 to 55 nm, preferably 10 to 50 nm.

In general, the noble metal nanoparticles can be any shape known to one of ordinary skill in the art. Examples of suitable shapes the noble metal nanoparticles may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplatelets, nanodisks, rods (also known as nanorods), and mixtures thereof. In the case of nanorods, the rod shape may be defined by a ratio of a rod length to a rod width, the ratio being known as the aspect ratio. Nanorods may have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires.

In some embodiments, the noble metal nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of noble metal nanoparticles having a different shape. As used herein, the term "non-uniform shape" refers to an average consistent shape that differs by more than 10% of the distribution of noble metal nanoparticles having a different shape. In one embodiment, the shape is uniform and at least 90% of the noble metal nanoparticles maybe spherical or substantially circular, and less than 10% are polygonal. In another embodiment, the shape maybe non-uniform and less than 90% of the noble metal nanoparticles are spherical or substantially circular, and greater than 10% are polygonal.

The size may refer to a diameter if the noble metal nanoparticles are spherical. The size may refer to the diameter of a circumsphere if the noble metal nanoparticles are polyhedral. In some embodiments, the size may refer to a mean distance from the surface of the noble metal nanoparticle to the centroid or center of mass of the noble metal nanoparticle. In alternative embodiments, the size may refer to a maximum distance from the surface of the noble metal nanoparticle to the centroid or center of mass of the noble metal nanoparticle. In some embodiments where the noble metal nanoparticles have an anisotropic shape such as nanorods, noble metal nanoparticle size may refer to a length of the nanorod, a width of the nanorod, an average of the length and width of the nanorod. In some embodiments in which the noble metal nanoparticles have non-spherical shapes, the noble metal nanoparticles' size refers to the diameter of a sphere having an equivalent volume as the noble metal nanoparticles. In some embodiments in which the noble metal nanoparticles have non-spherical shapes, the noble metal nanoparticles size refers to the diameter of a sphere having an equivalent diffusion coefficient as the noble metal nanoparticles.

In some embodiments, the noble metal nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the noble metal nanoparticles of the present disclosure are monodisperse having a particle size distribution ranging from 80% of the average particle size to 120% of the average particle size, preferably 90 to 110%, preferably 95 to 105% of the average particle size. In some embodiments, the noble metal nanoparticles are not monodisperse.

In general, the size of the noble metal nanoparticles may be determined by any suitable method known to one of ordinary skill in the art. In some embodiments, the size is determined by powder X-ray diffraction (PXRD). Using PXRD, the size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the noble metal nanoparticle size. For accurate size measurement by PXRD, the noble metal nanoparticle should be crystalline, comprise only a single crystal, and lack non-crystalline portions. Typically, the crystallite size underestimates noble metal nanoparticle size compared to other measures due to factors such as amorphous regions of noble metal nanoparticle, the inclusion of non-crystalline material on the surface of noble metal nanoparticle such as bulky surface ligands, and noble metal nanoparticle which may be composed of multiple crystalline domains. In some embodiments, the size of the noble metal nanoparticle is determined by dynamic light scattering (DLS). DLS is a technique which uses the time-dependent fluctuations in light scattered by particles in suspension or solution in a solvent, typically water to measure a size distribution of the noble metal nanoparticle. Due to the details of the DLS setup, the technique measures a hydrodynamic diameter of the noble metal nanoparticle, which is the diameter of a sphere with an equivalent diffusion coefficient as the noble metal nanoparticle. The hydrodynamic diameter may include factors not accounted for by other methods such as non-crystalline material on the surface of the noble metal nanoparticle such as bulky surface ligands, amorphous regions of particles, and surface ligand-solvent interactions. Further, the hydrodynamic diameter may not accurately account for non-spherical noble metal nanoparticle shapes. DLS does have an advantage of being able to account for or more accurately model solution or suspension behavior of the noble metal nanoparticle compared to other techniques. In some embodiments, the noble metal nanoparticle size is determined by electron microscopy techniques such as scanning electron microscopy (SEM) or transmission electron microscopy (TEM).

The porous oxide layer comprises transition metal oxide nanoparticles. In general, the transition metal oxide nanoparticles should be semiconducting transition metal oxide nanoparticles. Any semiconducting transition metal oxide may be used, examples of which include, but are not limited to zinc oxide, titanium dioxide, copper oxide (both CuO and $Cu_2O$), tin dioxide, iron (II) oxide, nickel oxide, and mixtures thereof. Further, as used herein, transition metal oxide also refers to materials which comprise both a transition metal and oxygen and which further comprise non-transition metals, such as alkaline earth metals or alkali metals. Examples of such materials include, but are not limited to barium titanate, strontium titanate, lithium niobate, lanthanum calcium manganite, and mixtures thereof. In some embodiments, the transition metal oxide nanoparticles are zinc oxide nanoparticles. The zinc oxide may be any suitable phase of zinc oxide, such as sphalerite (cubic), matraite (trigonal), or wurtzite (hexagonal). In preferred embodiments, the zinc oxide is wurtzite zinc oxide. In some embodiments, the zinc oxide nanoparticles are crystalline by PXRD.

In some embodiments, the transition metal oxide nanoparticles have a mean particle size of 10 to 50 nm, preferably 12.5 to 40 nm, preferably 15 to 35 nm, preferably 17.5 to 30 nm, preferably 20 to 27.5 nm, preferably 22.5 to 25 nm. The particle size may be determined as described above. In some embodiments, the transition metal oxide nanoparticles of the present disclosure are monodisperse, having a coefficient of variation or relative standard deviation, expressed as a percentage and defined as the ratio of the particle size standard deviation (σ) to the particle size mean (μ) multiplied by 100 of less than 25%, preferably less than 10%, preferably less than 8%, preferably less than 6%, preferably less than 5%, preferably less than 4%, preferably less than 3%, preferably less than 2%. In some embodiments, the transition metal oxide nanoparticles of the present disclosure are monodisperse having a particle size distribution ranging from 80% of the average particle size to 120% of the average particle size, preferably 90 to 110%, preferably 95 to 105% of the average particle size. In some embodiments, the transition metal oxide nanoparticles are not monodisperse.

In some embodiments, the zinc oxide nanoparticles are present in the porous oxide layer as agglomerates. In some embodiments, the agglomerates have a mean size of 150 to 300 nm, preferably 160 to 290 nm, preferably 165 to 285 nm, preferably 170 to 280 nm, preferably 175 to 275 nm, preferably 180 to 270 nm, preferably 185 to 265 nm, preferably 190 to 260 nm, preferably 195 to 255 nm, preferably 200 to 250 nm.

The porous oxide layer has a mean pore size of 2 to 30 nm, preferably 2.5 to 27.5 nm, preferably 5 to 25 nm, preferably 7.5 to 22.5 nm, preferably 10 to 20 nm. In some embodiments, the pores are present as voids formed between adjacent zinc oxide nanoparticles. Such voids may be formed in agglomerates of zinc oxide nanoparticles.

In general, the shape description above for the noble metal nanoparticles may apply to the transition metal oxide nanoparticles. In some embodiments, the transition metal oxide nanoparticles have substantially the same shape as the noble metal nanoparticles. In some embodiments, the transition metal oxide nanoparticles have a different shape from the noble metal nanoparticles. The noble metal nanoparticles may be centered above substantially the same point or portion of the solid support.

In some embodiments, a coverage density of noble metal nanoneedles present on the zinc oxide is $1 \times 10^8$-$10 \times 10^8$ particles/cm$^{-2}$, preferably $2 \times 10^8$-$8 \times 10^8$ particles/cm$^{-2}$, preferably $4 \times 10^8$-$6 \times 10^8$ particles/cm$^{-2}$.

In some embodiments, a coverage density of noble metal nanorings present on the zinc oxide is $5 \times 10^3$-$12 \times 10^3$ particles/cm$^{-2}$, preferably $6 \times 10^3$-$11 \times 10^3$ particles/cm$^{-2}$, preferably $7 \times 10^3$-$9 \times 10^3$ particles/cm$^{-2}$ and the noble metal nanorings are present as annular clusters of 2-20 silver nanorings, preferably 3-15 silver nanorings, preferably 6-10 silver nanorings.

In an embodiment, the surface-enhanced Raman scattering-active electrode has 1-12 times, preferably 1-11 times, preferably 1-10 times, preferably 1-9 times, preferably 1.2-8 times greater enhancement in surface-enhanced Raman scattering activity is obtained when the SERS active electrode includes the noble metal nanorings in comparison to the noble metal nanoneedles.

The surface-enhanced Raman scattering-active electrode may have a band gap of greater than 2.2 to 4 eV, preferably 2.4 to 3.28 eV, preferably 2.6 to 3.26 eV, preferably 2.8 to 3.24 eV, preferably 3.0 to 3.22 eV, preferably 3.1 eV.

According to another aspect, the present disclosure relates to a method of making the surface-enhanced Raman scattering (SERS)-active electrode. The method comprising depositing the porous oxide layer onto the solid support to form a first oxide-coated support, depositing a layer of the noble metal onto the first oxide-coated support to form a second-coated support, and annealing the second-coated support at 400 to 800° C., preferably 440 to 790° C., preferably 500 to 770° C., preferably 510 to 750° C., preferably 520 to 740° C., preferably 530 to 730° C., preferably 540 to 720° C., preferably 550 to 710° C., preferably 570 to 710° C., preferably 600 to 700° C. to form the surface-enhanced Raman scattering-active electrode.

In some embodiment, wherein the noble metal is selected from the group consisting of gold, platinum, palladium, ruthenium, rhodium, osmium, silver, copper, mercury, rhenium, iridium, and alloys thereof.

In some embodiment, wherein the solid support is glass, the noble metal is silver, and the transition metal oxide nanoparticles are wurtzite zinc oxide nanoparticles.

According to a preferred embodiment of the present disclosure, the method of making the SERS active electrode includes techniques such as sputtering.

For purposes of the invention, "sputtering" is a process whereby atoms, such as metallic atoms, are ejected from a solid target material due to bombardment of the target by energetic particles of a gas or a plasma in a vacuum chamber (sputtering chamber).

In an embodiment, the method includes depositing the porous oxide layer performed by direct current sputtering at a plasma power of 20 to 300 W, preferably 20 to 250 W, preferably 30 to 240 W, preferably 40 to 220 W, preferably 50 to 200 W for 5 to 100 minutes, preferably 6 to 90 minutes, preferably 7 to 80 minutes, preferably 8 to 70 minutes, preferably 10 to 60 minutes in oxygen gas and the transition metal to solid support distance is fixed at 2 to 40 cm, preferably 3 to 35 cm, preferably 4 to 30 cm, preferably 5 to 25 cm, preferably 5 to 23 cm, preferably 5 to 20 cm.

In some embodiments, the zinc oxide layer is deposited by DC reactive sputtering. Such DC reactive sputtering may be performed in an oxygen-comprising atmosphere. The method further includes sputtering a layer of a noble metal on the ZnO layer.

In some embodiments, the noble metal is deposited by DC sputtering.

In some embodiments, the layer of noble metal is sputtered at a plasma power of 1 to 100 W, preferably 2 to 80 W, preferably 3 to 60 W, preferably 4 to 50 W, preferably 5 to 40 W, preferably 5 to 30 W, preferably 5 to 20 W for 1 to 100 seconds, 1 to 90 seconds, preferably 1 to 80 seconds, preferably 1 to 70 seconds, preferably 1 to 60 seconds, preferably 1 to 50 seconds, preferably 1 to 30 seconds, preferably 1 to 20 seconds in argon gas.

In some embodiments, the layer of noble metal is sputtered at a base pressure and a working pressure of sputtering $1\times10^{-6}$ to $20\times10^{-6}$ torr, preferably $1\times10^{-6}$ to $18\times10^{-6}$ torr, preferably $1\times10^{-6}$ to $17\times10^{-6}$ torr, preferably $1\times10^{-6}$ to $15\times10^{-6}$ torr, preferably $1\times10^{-6}$ to $13\times10^{-6}$ torr, preferably $1\times10^{-6}$ to $10\times10^{-6}$ torr.

In an embodiment, annealing the second-coated support is performed under vacuum or inert atmosphere. Such an inter atmosphere may be provided by any suitable inert gas, such as nitrogen, helium, argon, neon, and the like.

In an embodiment, the method comprises annealing the second-coated support in argon gas at 400 to 900° C., preferably 450 to 850° C., preferably 480 to 800° C., preferably 490 to 780° C., preferably 490 to 750° C., preferably 500 to 700° C. for 0.25 to 5 hours, preferably 0.5 to 4 hours, preferably 0.75 to 3.5 hours, preferably 1 to 3 hours with a ramp of a heating rate of 5 to 35° C./min, preferably 6 to 34° C./min, preferably 7 to 33° C./min, preferably 9 to 31° C./min, preferably 10 to 30° C./min to form noble metal nanoneedles on the porous oxide layer.

In some embodiments, the method includes annealing the second-coated support in argon gas at 200 to 1100° C., preferably 300 to 1000° C., preferably 400 to 900° C., preferably 450 to 800° C., preferably 500 to 700° C. for 0.2 to 6 hours, preferably 0.5 to 6 hours, preferably 0.7 to 5 hours, preferably 0.8 to 4 hours, preferably 1 to 3 hours with a ramp of a heating rate of 1 to 60° C./min, preferably 2 to 50° C./min, preferably 5 to 40° C./min, preferably 10 to 30° C./min to form noble metal nanorings on the porous oxide layer.

According to another aspect, the present disclosure also relates to a method of obtaining a Raman spectrum of an analyte. The method includes depositing the analyte onto the SERS active electrode 1 to form a sample; exposing the sample to laser light such that a portion of the laser light is scattered by the sample to form scattered light, and detecting the scattered light.

In some embodiments, the analyte contacts at least one selected from the group consisting of the porous oxide layer, the noble metal nanoneedles, and the noble metal nanorings.

In some embodiments, the laser light has a wavelength of 522 to 542 nm, preferably 524 to 540 nm, preferably 526 to 538 nm, preferably 528 to 536 nm, preferably 530 to 534 nm, preferably 532 nm. In an embodiment, the noble metal nanorings have an enhancement factor of greater than $1\times10^6$ to $7\times10^6$, preferably $1\times10^6$ to $6\times10^6$, preferably $1.1\times10^6$ to $6\times10^6$, preferably $1.1\times10^6$ to $5.9\times10^6$.

The scattered Raman photon is collected through a slit in a backscattering configuration. The proportional relationship between Raman scattering intensity and analyte concentration is used to perform quantitative analysis.

In some embodiments, the analyte includes at least one biological molecule selected from the group consisting of a protein, a deoxyribonucleic acid sequence, a ribonucleic acid sequence, an amino acid, a peptide, a nucleotide, a nucleoside, and a neurotransmitter. In some embodiments, the analyte includes at least one synthetic molecule. In some embodiments, the analyte includes Rhodamine 6G.

EXAMPLES

The following examples are intended to further illustrate exemplary protocols for preparing SERS active electrode according to certain embodiments, and are not intended to limit the scope of the claims.

Fabrication and Topographic Confirmation

Ag NPs and Ag NRs were fabricated using a dual-beam automatic sputtering coater (model #NSC-4000) followed by subsequent treatment in a tubular furnace (model MTI Corporation GSL-1700X). High purity Zn (99.999%) and Ag (99.99%) targets were used as received from Semiconductor Wafer Inc. without any modification. The targets were pre-sputtered with a closed shutter for 1 min and clean glass slides were used as substrates. In brief, a thin layer of ZnO on the glass slide (called hereafter ZnO/Glass) was prepared by DC sputtering of Zn target at a plasma power of 100 W for 25 min in oxygen ($O_2$) gas flow of 80 cubic centimeters per minute at STP (sccm). Subsequently, an ultrathin layer of Ag was sputtered atop at plasma power of 10 W for 5 secs in Ar gas flow of 80 sccm. In both cases, base pressure and working pressure in the sputtering chamber were maintained at $\sim2\times10^{-6}$ torr and $\sim7\times10^{-6}$ torr, respectively. The target to substrate distance was fixed at 10 cm. An ultrathin layer of Ag on ZnO/Glass was transferred immediately to a tubular furnace to fabricate Ag NPs on ZnO/Glass (called hereafter Ag NPs-ZnO) and Ag NRs on ZnO/Glass (called hereafter Ag NRs-ZnO). Ag NPs-ZnO/Glass was achieved by further treatment in continuous Ar gas flow at 600° C. for 2 hrs with a ramp of a heating rate of 20° C./min. As for Ag NRs-ZnO/Glass, the treatment was carried out in continuous $N_2$ gas flow at 700° C. for 2 hrs with a ramp of a heating rate of 20° C./min. Topographic confirmation and in-depth morphology of Ag NPs-ZnO, Ag NNs-ZnO and Ag NRs-ZnO were carried out using high-resolution FESEM (model #Tescan LYRA3). To the best of our knowledge, Ag NNs-ZnO were fabricated for the first time in a physical deposition technique, and SERS-activity was evaluated thereof under this investigation. The specimens studied in this investigation allow us to validate the impact of EM near-field in SERS enhancements in a presence of 0D, 1D and 2D plasmonic SERS-active substrates.

The coverage density of Ag NPs-ZnO, Ag NNs-ZnO and Ag NRs-ZnO was estimated to be ~4×10$^{10}$, ~5×10$^8$ and ~8×10$^3$ particles/cm$^{-2}$ respectively. The as-fabricate Ag NPs-ZnO, Ag NNs-ZnO and Ag NRs-ZnO were investigated by high-resolution FESEM followed by SERS measurements to verify the SERS activity of the same. It is noted that Ag NPs-ZnO were found to be in various sizes, although the shape was mostly spherical, whereas Ag NNs-ZnO were found mostly uniform shape. In the case of Ag NRs, instead of a perfect ring structure, the as-fabricated Ag NRs-ZnO were found to be of various shapes and sizes along with fractal features at the edges.

Figure 1B:
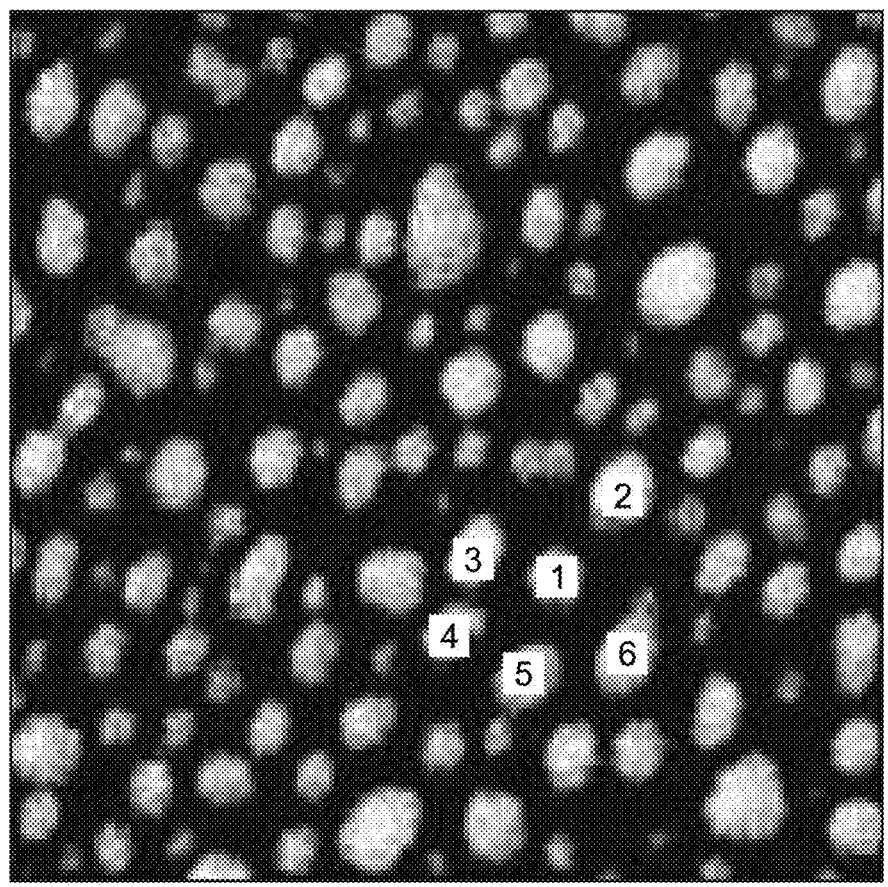
FIG. 1B illustrates enlarged view of a small area as marked by a white dotted square in FIG. 1A.
Figure 1C:
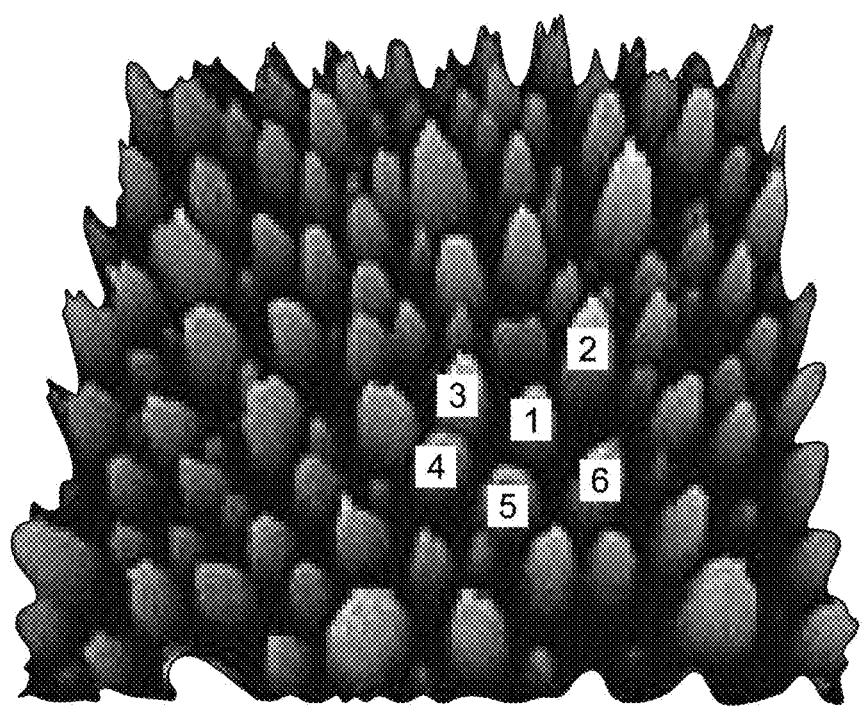
FIG. 1C illustrates a Hawk-eye view (3D) of a small area FIG. 1B.
Figure 1D:
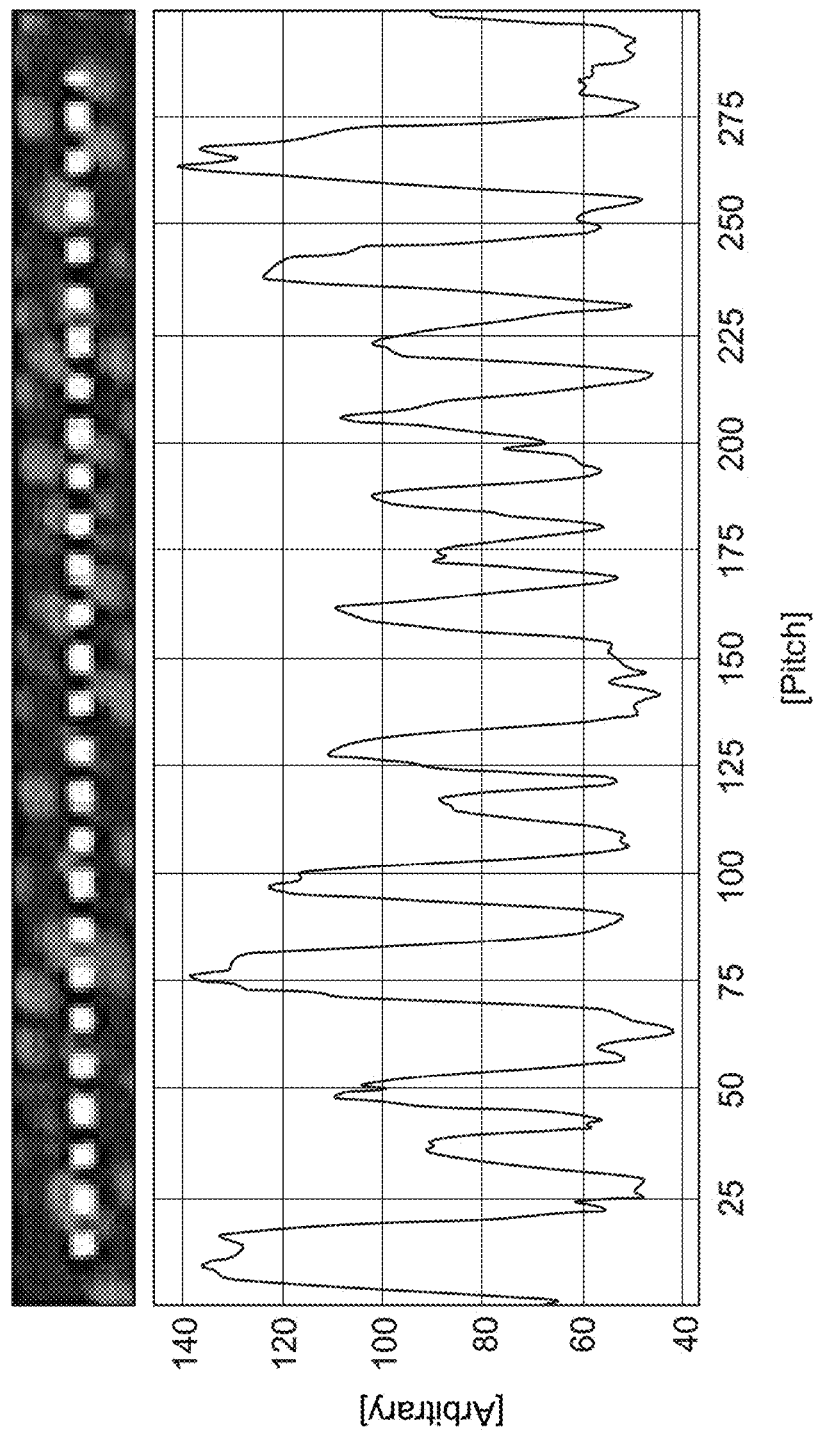
FIG. 1D illustrates a Line profile along the white dotted line crossing 14 Ag NPs-ZnO as shown in FIG. 1A.
Figure 1E:
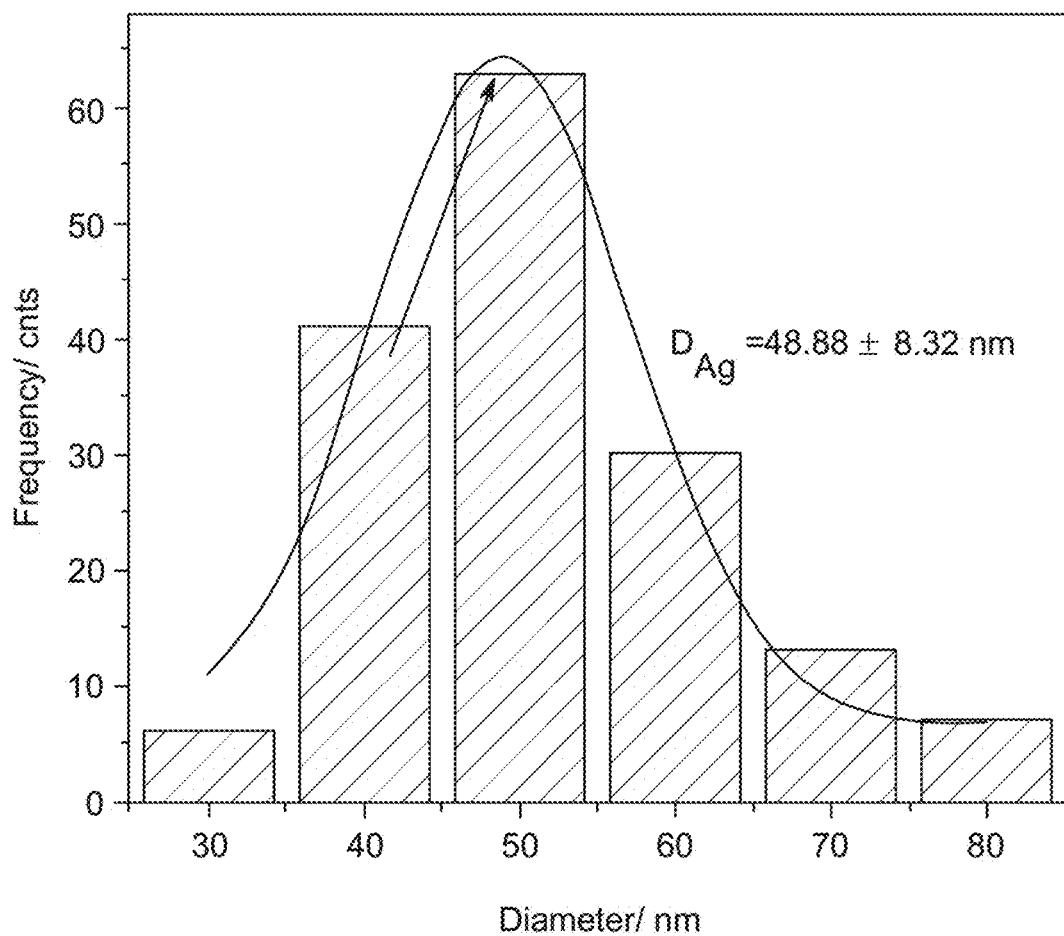
FIG. 1E illustrates size distribution (bar graph) of Ag NPs-ZnO along with Gaussian fit (curve), according to certain embodiments.

FIG. 1A shows a high-resolution FESEM micrograph of the Ag NPs-ZnO. Ag NPs-ZnO of various sizes, but mostly spherical have been observed in this regard. A zoom-in view of the same image has been further investigated as shown in FIG. 1B. FIG. 1B represents a magnified view (1 μm×1 μm) as marked by the white dotted square in FIG. 1A. It is noteworthy that the as-fabricated Ag NPs-ZnO were found to be in different sizes and different interparticle gaps. A 3D hawk-eye view of the same zoom-in view image has been shown in FIG. 1C. Six typical Ag NPs-ZnO as marked by 1, 2, 3, 4, 5 and 6 in FIG. 1B and FIG. 1C were further investigated and mentioned in insets. Most of the nanoparticles were found to be spherical in addition to a few elliptical and arbitrary shape nanoparticles. Insets (i)-(vi) display the same six typical Ag NPs-ZnO as marked by 1, 2, 3, 4, 5, and 6 in FIG. 1B and FIG. 1C along with approximate shape and dimensions. The white dotted boundary of each nanoparticle indicates the approximate edge of the corresponding nanoparticles. The dimensions along white dotted lines of insets (i)-(vi) were estimated to be 62, 65, 56, 52, 56, and 55 nm, respectively. FIG. 1D displays a line profile along the white dotted line as shown in FIG. 1A. Dips D1 and hills H1 and the distances between such dips D1 and hills H1 clarified further that the as-fabricated Ag NPs-ZnO were of different sizes and different interparticle gaps. The Ag NPs-ZnO across the white dotted line were further shown as an inset of FIG. 1D. Based on more than 150 events as observed in a FESEM micrograph (FIG. 1B), a histogram was obtained to figure out the size distribution of such Ag NPs-ZnO. As shown in FIG. 1E, a relatively narrow size distribution, 48.88±8.32 nm using the Gaussian fit GF1 (curve) was estimated. The narrow full width at half maximum (FWHM) of 8.32 nm inferred that as-fabricated Ag NPs-ZnO were of nearly uniform size distribution as demonstrated and shown in insets of FIG. 1B. It is to be noted that such narrow size distribution, 48.88±8.32 nm is indeed suitable for achieving higher SERS enhancements. The details will be demonstrated in the latter part of the text.

Figure 2A:
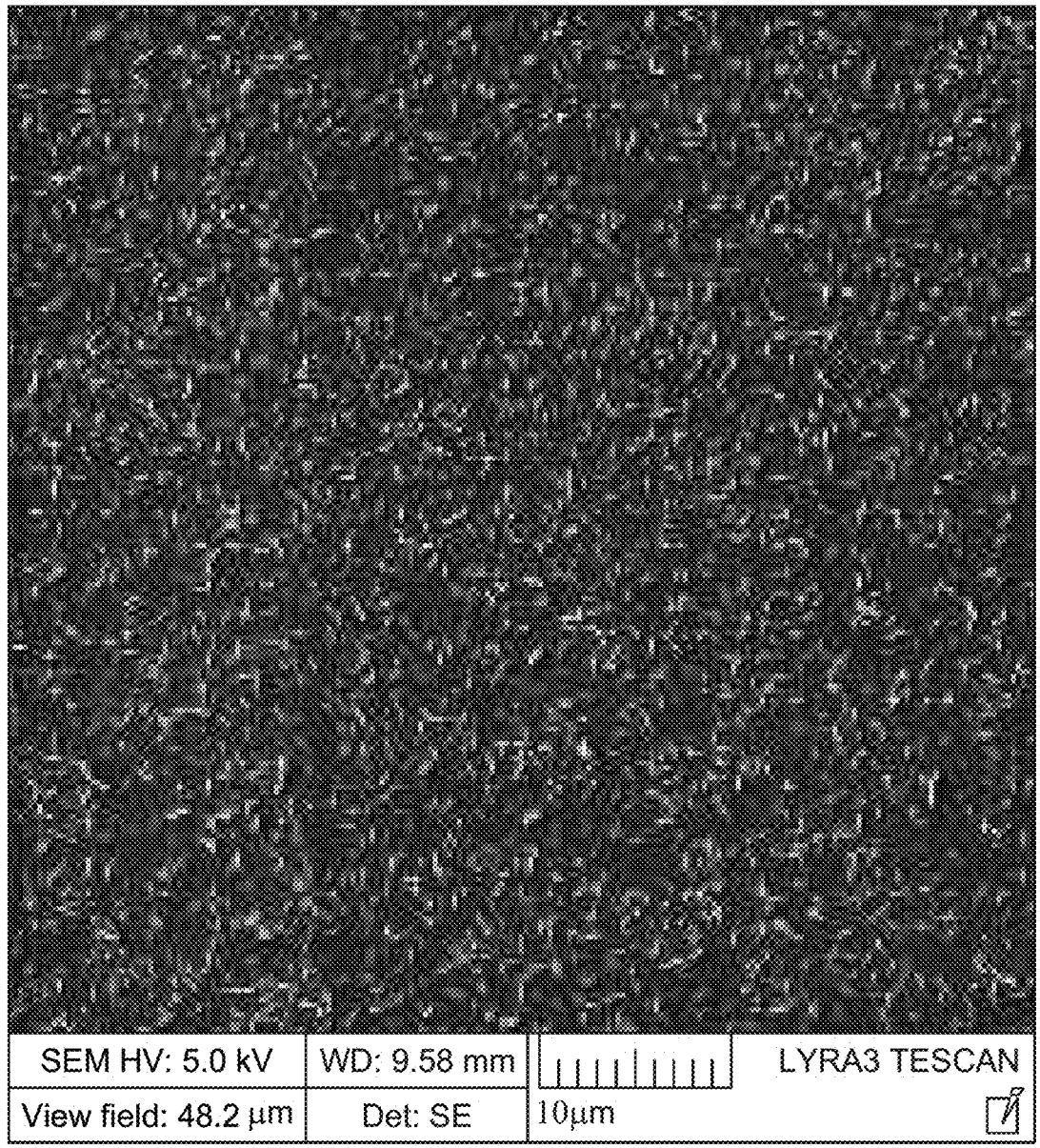
FIG. 2A illustrates FESEM micrograph of Ag NNs-ZnO, according to certain embodiments.
Figure 2B:
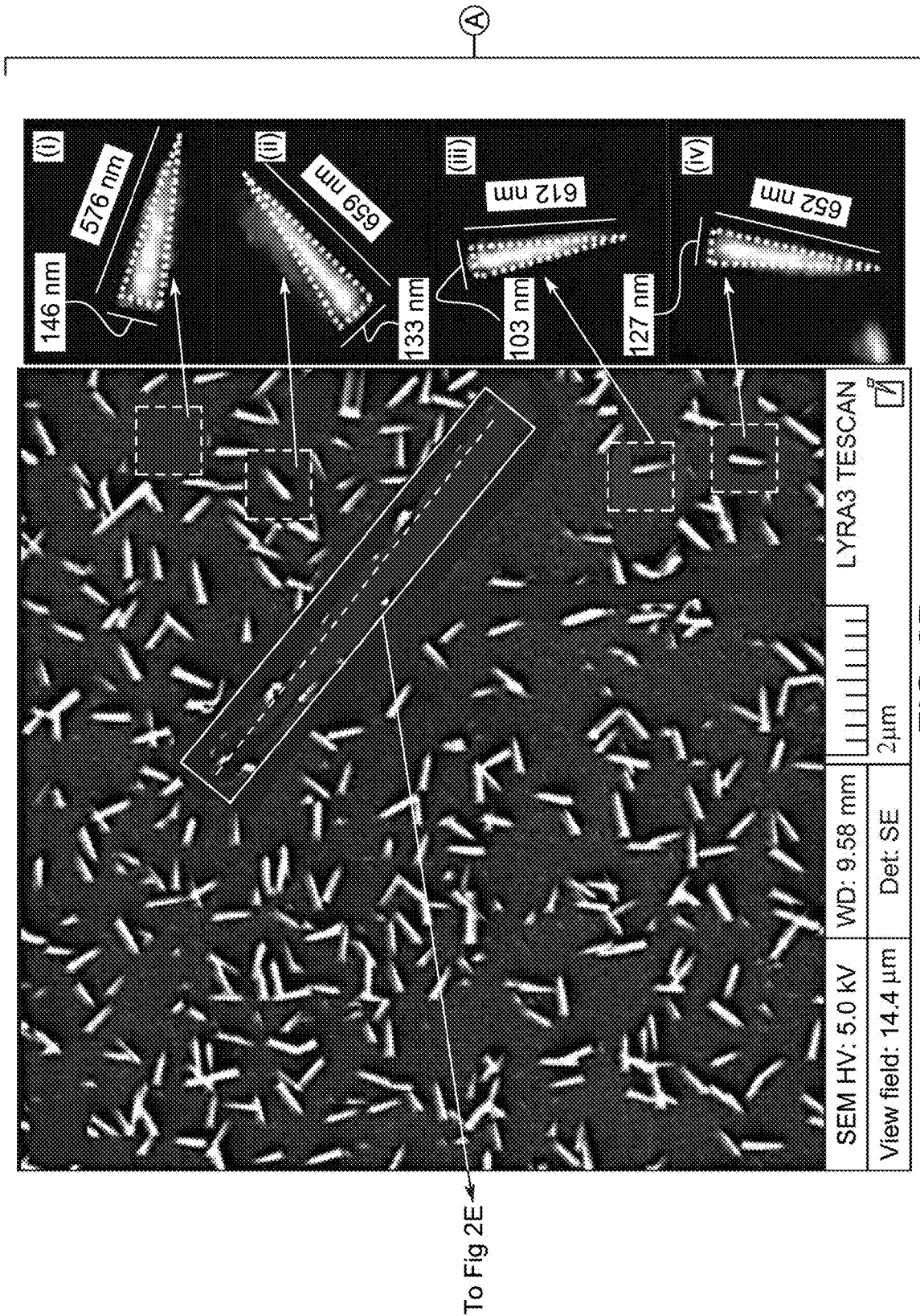
FIG. 2B illustrates a high-resolution FESEM micrograph of FIG. 2A.
Figure 2C:
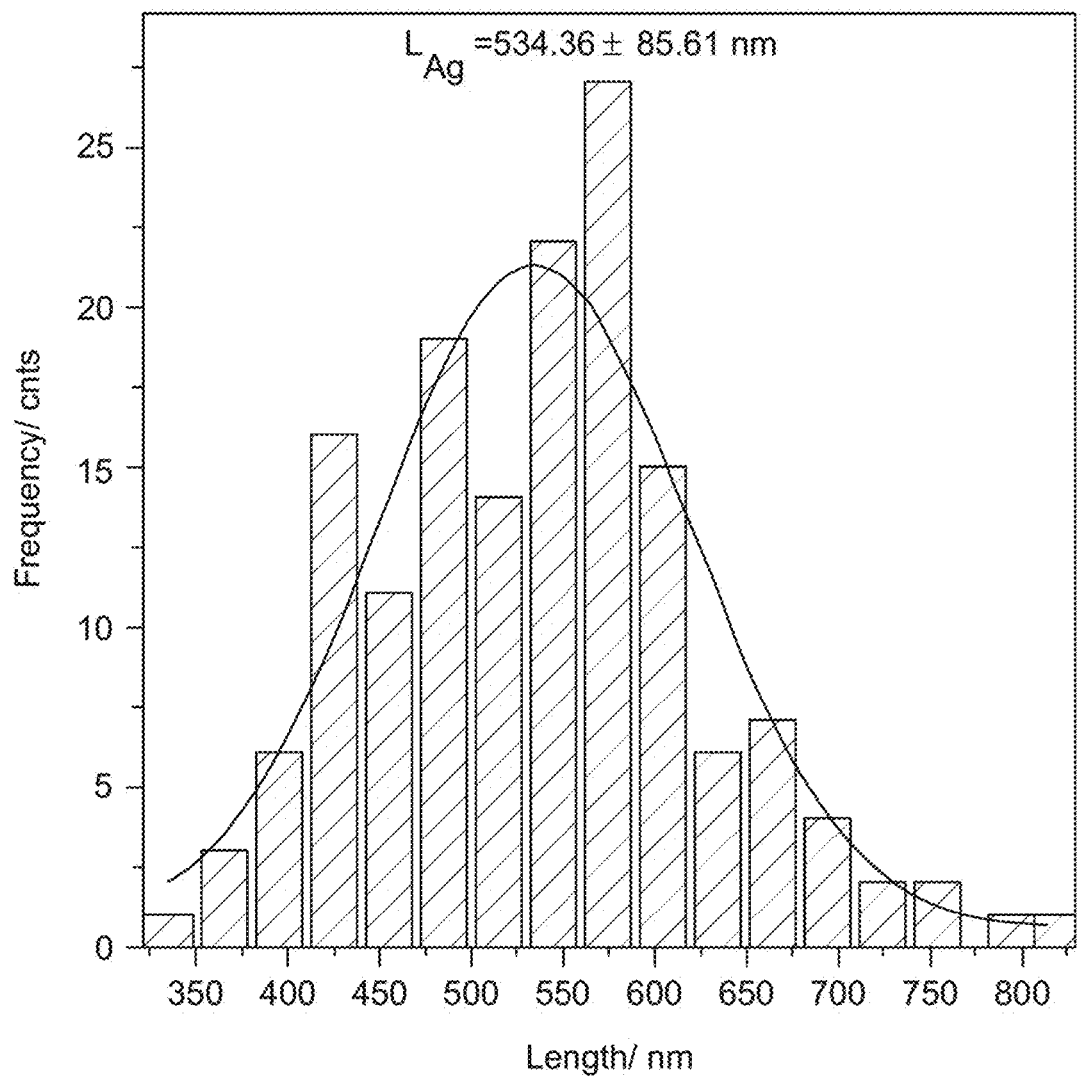
FIG. 2C illustrates size distributions (bar graph) of Ag NNs-ZnO's lengths along with Gaussian fit (curve) along the white dotted line crossing ten Ag NNs-ZnO as shown in FIG. 2B.
Figure 2D:
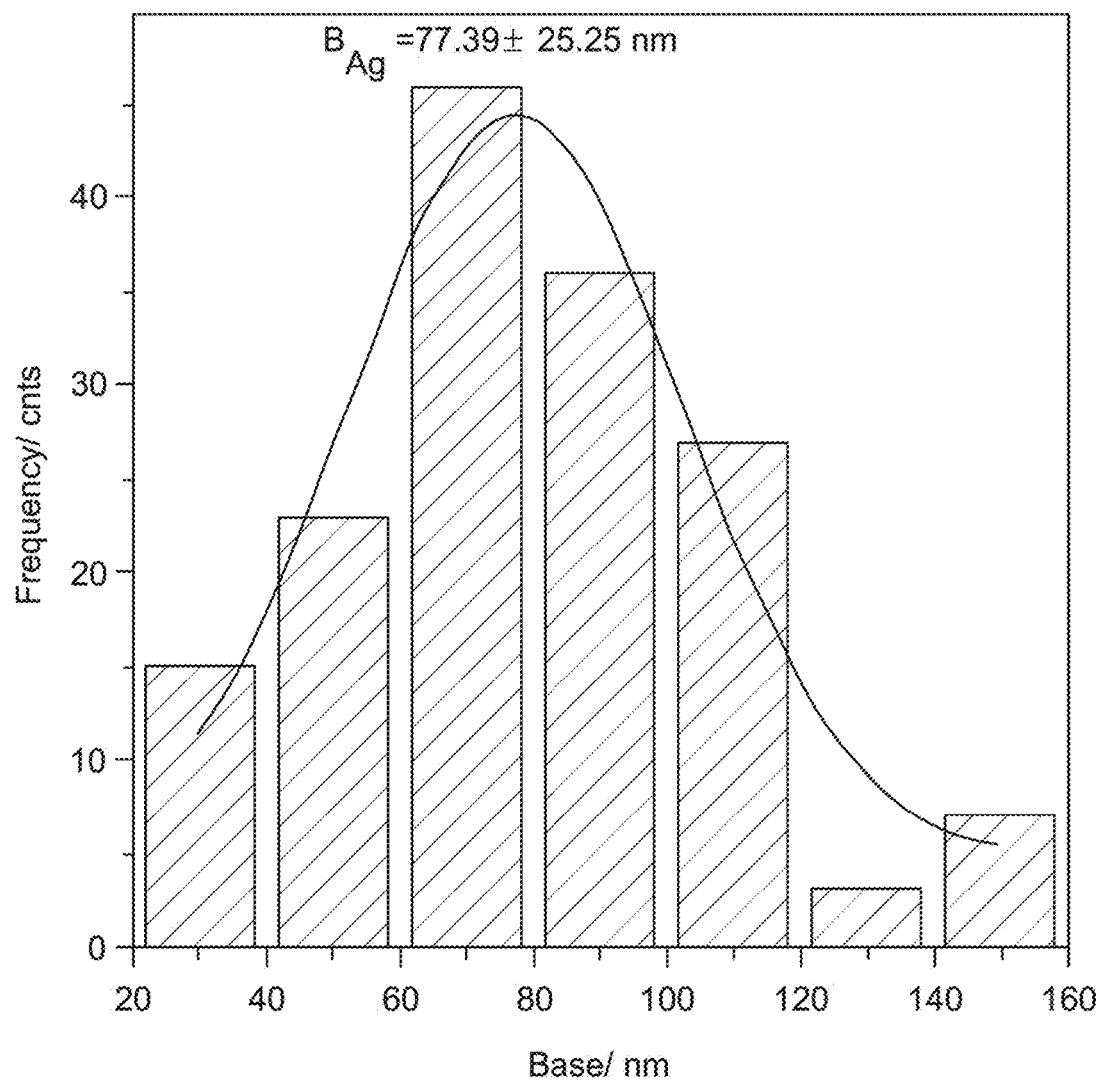
FIG. 2D illustrates size distributions (bar graph) of Ag NNs-ZnO's bases along with Gaussian fit (curve) along the white dotted line crossing ten Ag NNs-ZnO as shown in FIG. 2B.
Figure 2E:
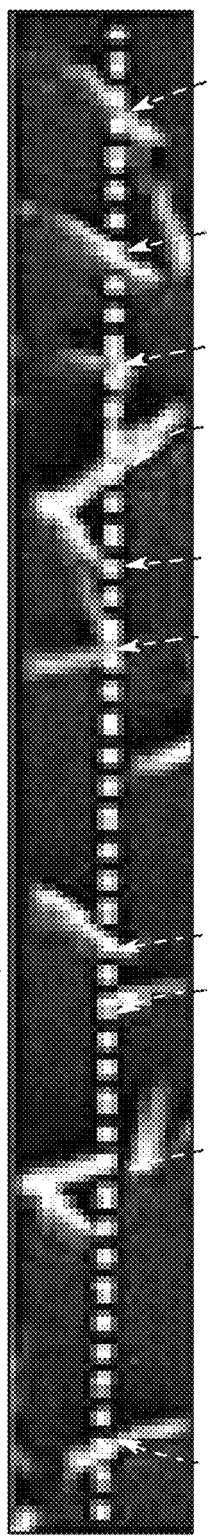
FIG. 2E illustrates a Line profile along the white dotted line crossing ten Ag NNs-ZnO as shown in FIG. 2B.
Figure 2E:
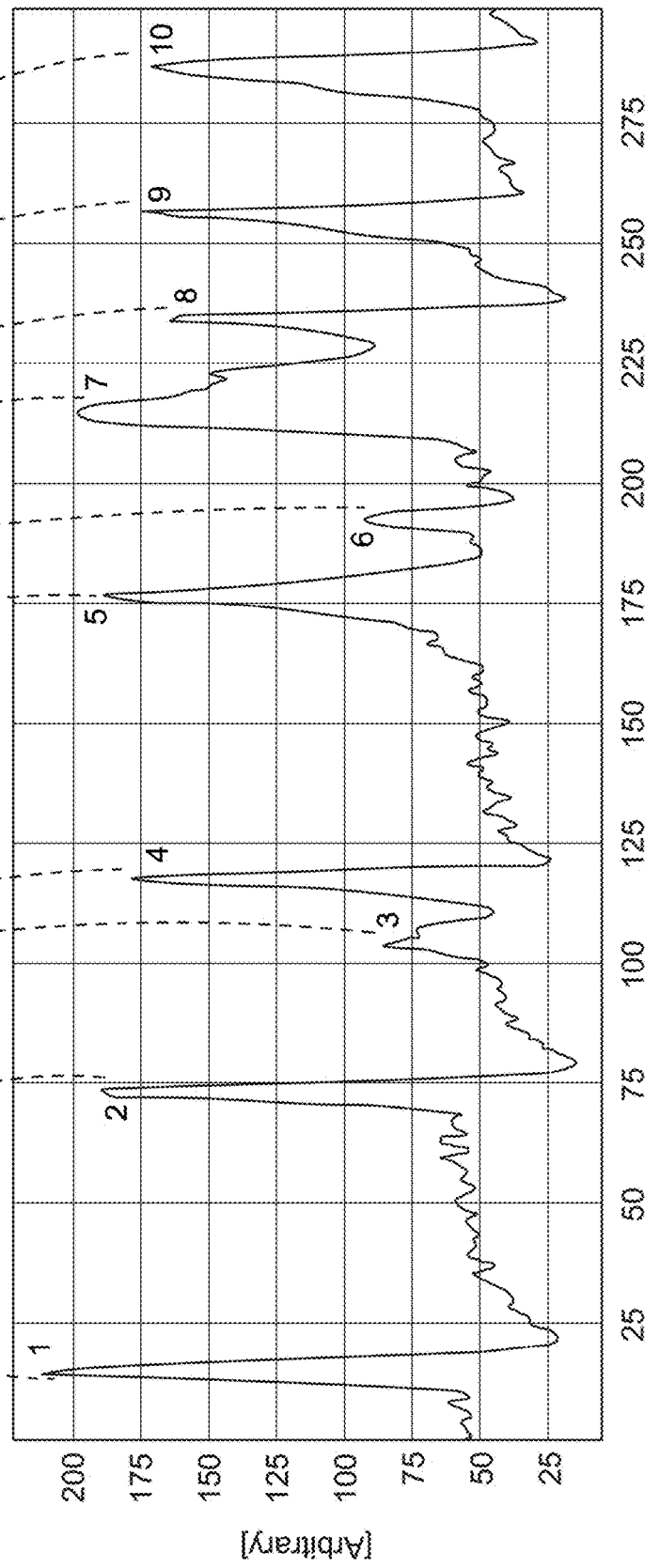

1D nanoparticles are well-known for the "lightening rod" effect; a phenomenon where the local EM near-field confines at both edges. In such a scenario, the target analyte gets more opportunity to be within SHSs and thus SERS with higher EF is expected. Contrary to a nanorod or nanowire, a NN possesses a sharp edge on one side and four edges on the other side near the base. FIG. 2A shows a low-resolution FESEM micrograph of Ag NNs-ZnO with a coverage density of ~5×10$^8$ particles/cm$^{-2}$. A high-resolution FESEM micrograph of the same is shown in FIG. 2B. As-fabricated Ag NNs-ZnO were found to be in different lengths and bases in addition to different directions, as shown in FIG. 2B. To understand further in-depth topography, four typical Ag NNs-ZnO of different directions were selected and marked as white dashed squares in FIG. 2B and corresponding details were mentioned in insets (i)-(iv). Estimated lengths and bases of selected Ag NNs-ZnO were observed to be 576 and 146 nm, 659 and 133 nm, 612 and 103 nm and 652 and 127 nm as mentioned in insets (i)-(iv), respectively. Insets (v)-(viii) represent 3D hawk-eye views of the individual Ag NNs-ZnO as shown in insets (i)-(iv), respectively. Based on more than 150 events as observed in a FESEM micrograph (FIG. 2B), a histogram was obtained to figure out the length and base distribution of such Ag NNs-ZnO. As shown in FIG. 2C, a relatively broadened length distribution, 534.36±85.61 nm using the Gaussian fit GF2 (curve) was estimated. On the other hand, a relatively narrow base distribution, 77.39±25.25 nm using the Gaussian fit GF3 (curve) was estimated as shown in FIG. 2D. FIG. 2E displays a line profile along the white dotted line as shown in FIG. 2B. A zoom-in view of the ten Ag NNs-ZnO crossed by the white dotted line was further shown as an inset of FIG. 2D.

Figure 3A:
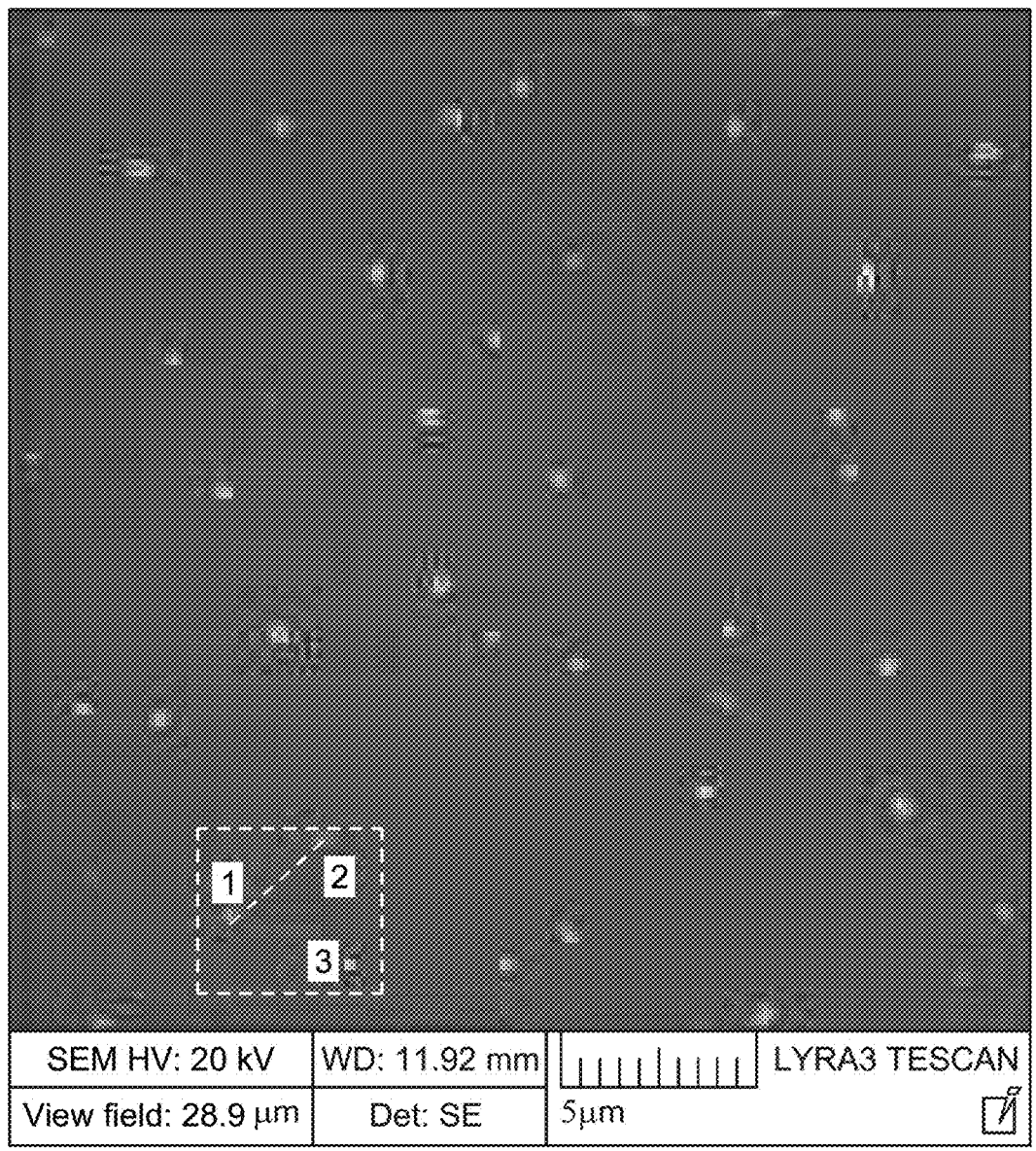
FIG. 3A illustrates FESEM micrograph of Ag NRs-ZnO, according to certain embodiments.
Figure 3B:
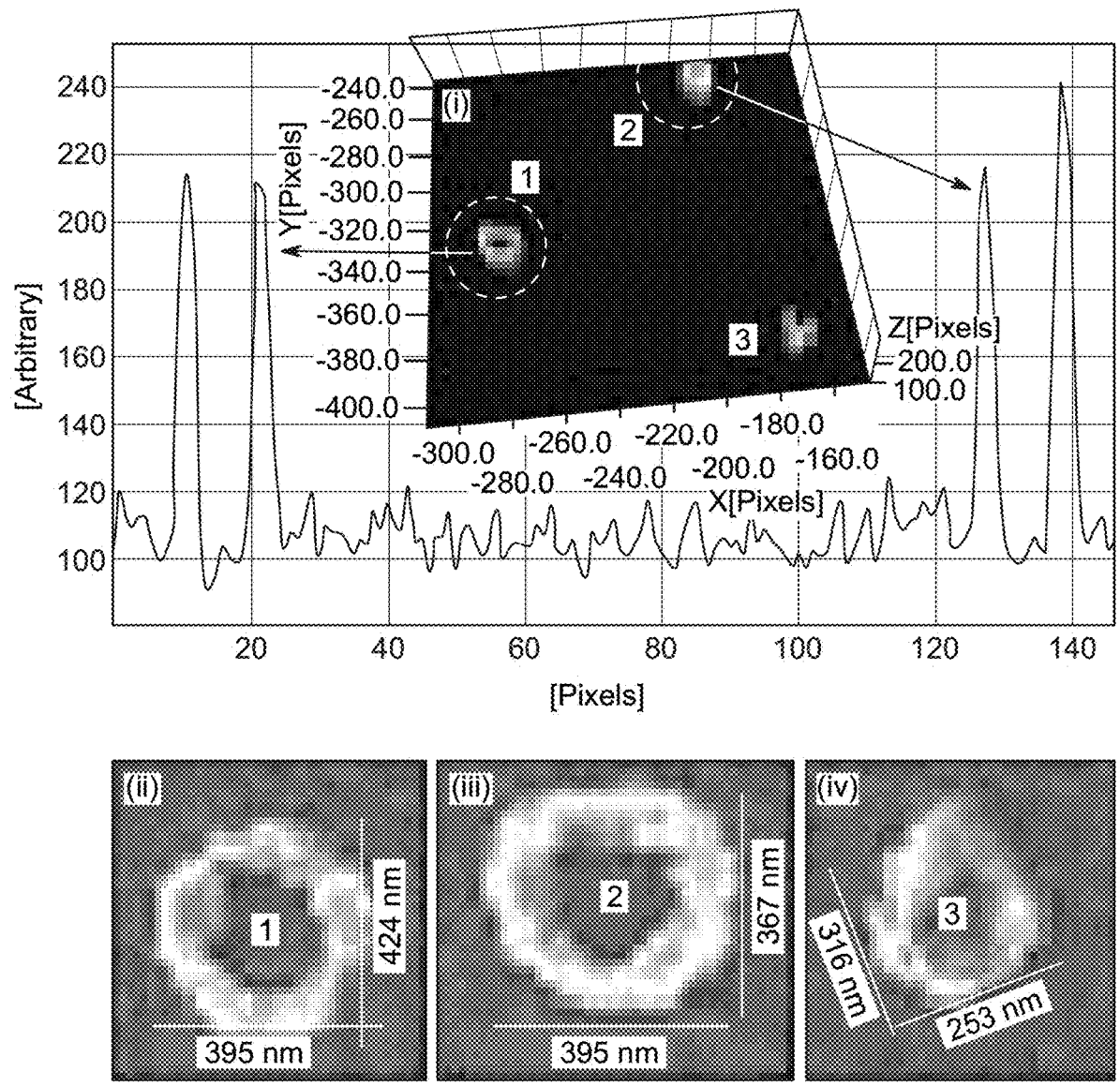
FIG. 3B illustrates a Line profile along a black dotted line crossing two Ag NRs-ZnO marked by "1" and "2" within a white dotted square in FIG. 3A. (i): Hawk-eye view (3D) of a zoom-in area (5 µm×5 µm) as marked by white dotted square in FIG. 3A and three typical Ag NRs-ZnO are marked by "1", "2' and "3" therein. (ii)-(iv): Three high-resolution Ag NRs-ZnO as marked by "1", "2' and "3" in FIG. 3A.

Ag NRs of metal and metal oxide had been reported in SERS where most of the studies focused on smooth NRs and the corresponding EM distributions were demonstrated straightforward. The NRs were considered perfect in circular shape along with smooth edges. However, the EM near-field distribution depends heavily on nanometric local structure, the incident polarization as well as interparticle gaps. Here in this investigation, the edge of Ag NRs-ZnO was found a neither smooth nor linear aggregation of NPs. FESEM micrographs confirmed that the as-fabricated Ag NRs-ZnO consisted of clusters of different sizes and shapes. FIG. 3A represents a typical low-resolution FESEM micrograph of Ag NRs-ZnO. Most of the Ag NRs-ZnO were of different shapes and sizes wherein some were circular and elliptical in shapes, and others were found arbitrary and unpredictable in shape. It is noteworthy that the height of the edges of Ag NRs-ZnO was observed to be different as well. A line profile along the black dotted line crossing two Ag NRs-ZnO marked by "1" and "2" within the white dotted square in FIG. 3A was shown in FIG. 3B. Inset (i) of FIG. 3B represents hawk-eye view (3D) of a zoom-in area (5 μm×5 μm) as marked by the white dotted square in FIG. 3A and three typical Ag NRs-ZnO are marked by "1", "2' and "3" therein. The two bumps on the left of the line profile indicate the heights of the edges of Ag NRs-ZnO marked by "1" in the inset (i), whereas the other two bumps on the right of the same line profile correspond to the heights of the edges of the Ag NRs-ZnO marked by "2". Further to reveal the in-depth topography, these three typical Ag NRs-ZnO as marked by "1", "2' and "3" in FIG. 3A and inset (i) of FIG. 3B were investigated. Insets (ii)-(iv) display zoom-in FESEM micrographs of Ag NRs-ZnO as marked by "1", "2' and "3" in FIG. 3A and inset (i) of FIG. 3B along with estimated dimensions. Diameters along the horizontal and vertical axes of Ag NRs-ZnO marked by "1", "2' and "3" in FIG. 3A and inset (i) of FIG. 3B were estimated to be 395 and 424 nm, 395 and 367 nm and 253 and 316 nm, respectively.

Figure 3C:
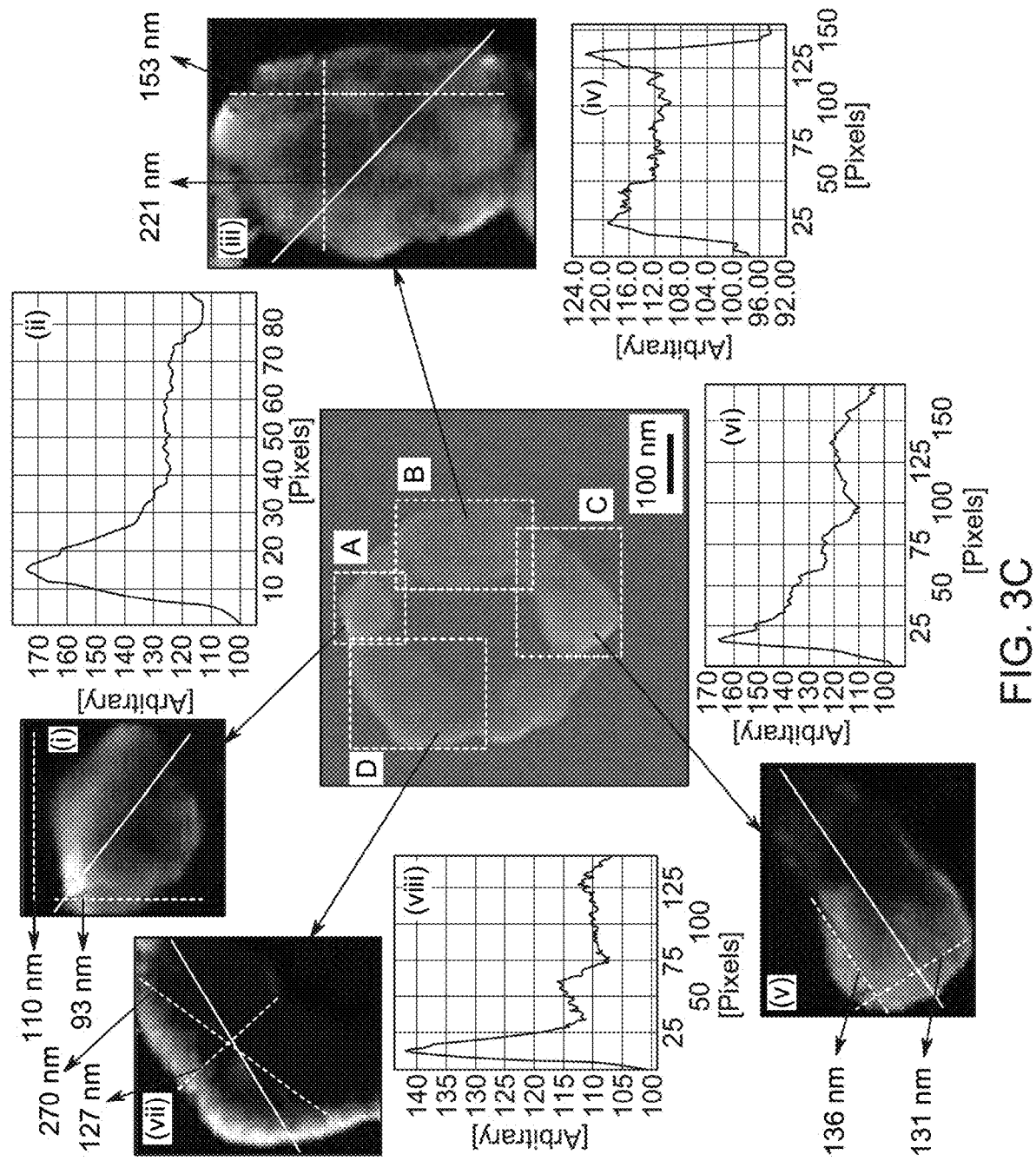
FIG. 3C illustrates a high-resolution FESEM micrograph of an individual Ag NR—ZnO indicating four typical segments marked by white dashed rectangles "A", "B", "C" and "D", according to certain embodiments. (i)-(ii): The segment marked by "A" indicating round shaped clusters along with dimensions therein and the line profile along the white dotted line mentioned in (i) respectively. (iii)-(iv): The segment marked by "B" indicating elongated shaped clusters along with dimensions therein and the line profile along the white dotted line mentioned in (iii) respectively. (v)-(vi): The segment marked by "C" indicating complex shaped clusters along with dimensions therein and line profile along the white dotted line mentioned (v) respectively. (vii)-(viii): The segment marked by "D" indicating complex shaped clusters along with dimensions therein and line profile along the white dotted line mentioned in (vii) respectively.

As mentioned earlier, EM near-field confinement that is responsible for giant SERS enhancement relies heavily on local nanometric topography. Therefore it is inevitable to understand the meticulous details of the Ag NRs-ZnO and correlate such topography to SERS enhancement and EM near-field distributions. A high-resolution FESEM micrograph as shown in FIG. 3C further revealed that individual Ag NRs-ZnO consisted of small Ag clusters. For the convenience of readers and to follow the in-depth analysis of Ag NRs-ZnO, four segments of interest were marked by white dashed rectangles "A", "B", "C" and "D" in FIG. 3C. Segment "A" represents a cluster of elliptical shapes as shown in inset (i) of FIG. 3A has horizontal and vertical lengths of 110 and 93 nm along the white dashed lines. Inset (ii) of FIG. 3A shows a line profile along the white dotted line as shown in the inset (i) of FIG. 3C. It was evident that the surface of such a cluster was not uniform. Segment "B" represents a cluster of complex shapes as shown in inset (iii) of FIG. 3C has horizontal and vertical lengths of 153 and 221 nm along the white dashed lines. Inset (iv) of FIG. 3C shows a line profile along the white dotted line as shown in the inset (iii) of FIG. 3C. The surface of such a cluster was found rough from place to place as revealed in the line profile. A further degree of a complex cluster consisting of several small grains was observed in segment "C". Inset (v) of FIG. 3C shows segment "C" having short and long dimensions of 131 and 136 nm along the white dashed lines mentioned therein. Inset (vi) of FIG. 3C shows a line profile along the white dotted line as shown in the inset (v) of FIG. 3C. Segment "D" represents a bigger cluster of arbitrary shapes as shown in inset (vii) of FIG. 3C having short and long dimensions of 127 and 270 nm along the white dashed lines. Inset (viii) of FIG. 3C shows a line profile along the white dotted line as shown in the inset (vii) of FIG. 3C. Considering the shapes and dimensions of the clusters and the arrangement of such clusters as shown in inset (i)-(viii) of FIG. 3C, it was speculated that the local EM near-field distributions would excel and thus enhanced SERS signals would be achieved. Indeed, the inherent features of the Ag NRs-ZnO facilitated achieving SERS enhancement factor higher compared to those obtained in Ag NPs-ZnO and Ag NNs-ZnO.

SERS-Activity

A SERS set-up was designed to demonstrate the SERS-activity of Ag NPs-ZnO, Ag NNs-ZnO and Ag NRs-ZnO. In-Situ Raman Spectrometer (Model #Horiba IHR-320) consisted of 10 m fiber optics and CCD was used to probe the specimen. Raman-active dye, R6G ($C_{28}H_{31}N_2O_3Cl$) was used as a standard probe. R6G was used as received from Chroma GesellschaftSchmid GMBH & Co. The specimens were incubated with R6G dye of $1 \times 10^{-6}$ M for ca. 10 mins and thereafter rinsed by deionized water copiously. An excitation of 532 nm was fed through an optical fiber and a long working distance lens (40×) was used to shine the specimens. The scattered Raman photon was collected through a slit of 40 µm in a backscattering configuration. The exposure time was maintained as 15 sec. and accumulation of 2 at a grating of 600 lines/mm for all the measurements. Air-cooled solid-state laser kits of 300 mW was used for 532 nm laser. To avoid dissociation or damage, the laser was filtered to 40% and turned off immediately after the signal collection. The experiments were conducted at ambient and normal atmospheric pressure.

In SERS enhancement, the EE mechanism is dominant and contributes as high as $10^6$ to $10^8$ times. LSPR-mediated giant EM near-field distributions (known as SHSs) around a plasmonic nanostructure are of particular interest in the EM mechanism. However, such confinement and localization occur at the interstitials of two plasmonic NPs or at the apex of a plasmonic nanostructure. Isolated spherical plasmonic nanoparticles show lower EM near-field distributions, whereas the "lightening rod" effect makes the 1D-nanostructures more favorable in localizing EM near-field distributions in two different sites. However, 2D-plasmonic nanostructures have been reported to have higher sites of EM near-field distributions compared to those observed in 0D and 1D plasmonic nanoparticles. In this context, Ag NPs-ZnO, Ag NNs-ZnO and Ag NRs-ZnO were considered as 0D-, 1D- and 2D-plasmonic nanostructures, respectively. The SERS-activities of such different dimensional nanostructures were demonstrated as shown in FIG. 4A through FIG. 4C.

Figure 4A:
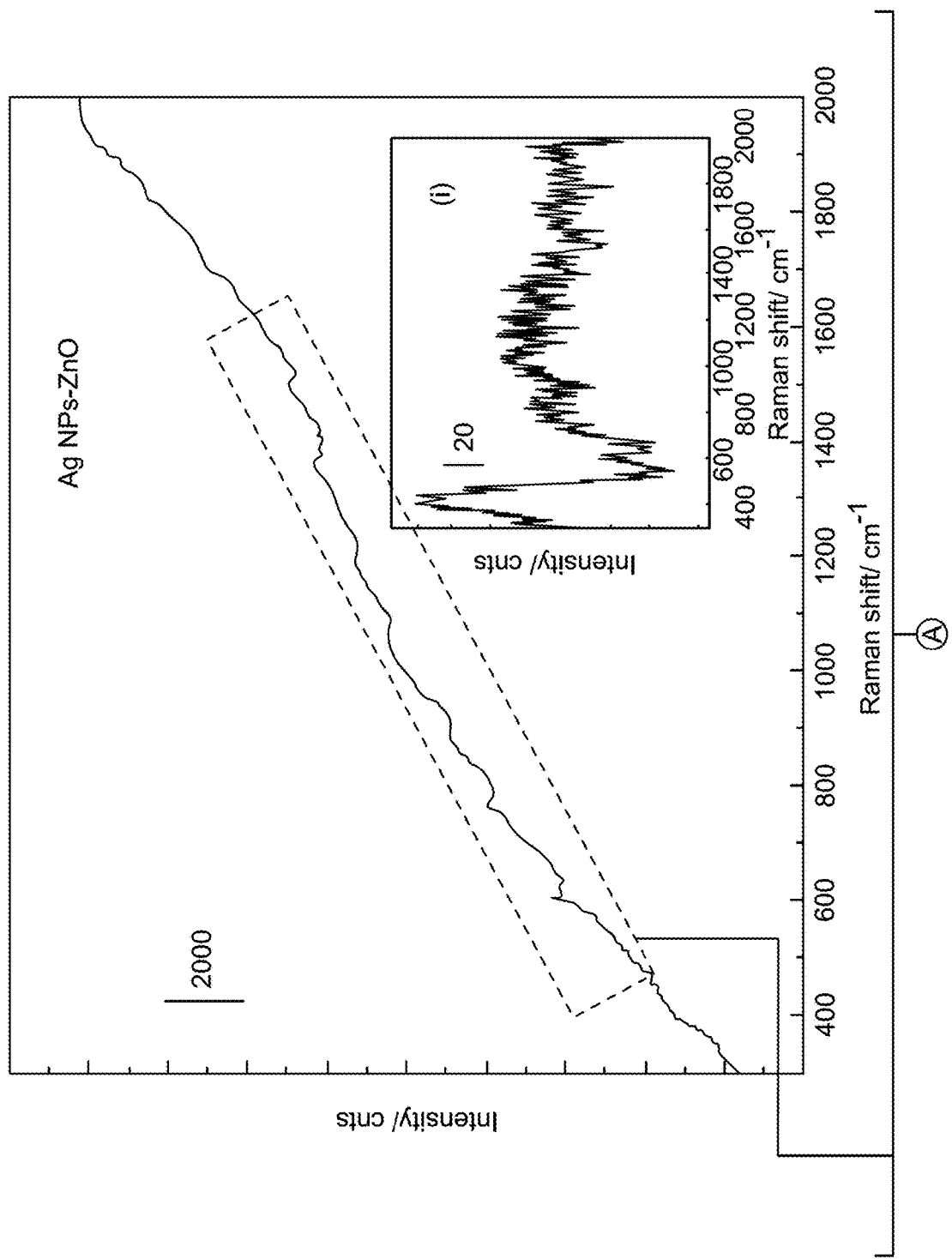
FIG. 4A illustrates SERS spectrum of R6G adsorbed on Ag NPs-ZnO, according to certain embodiments. (i): Raman spectrum of Ag NPs-ZnO without R6G (ii): Fluorescence background-subtracted SERS spectrum of R6G adsorbed on Ag NPs-ZnO along with eight bands marked by vertical dash-dotted lines.
Figure 4A:
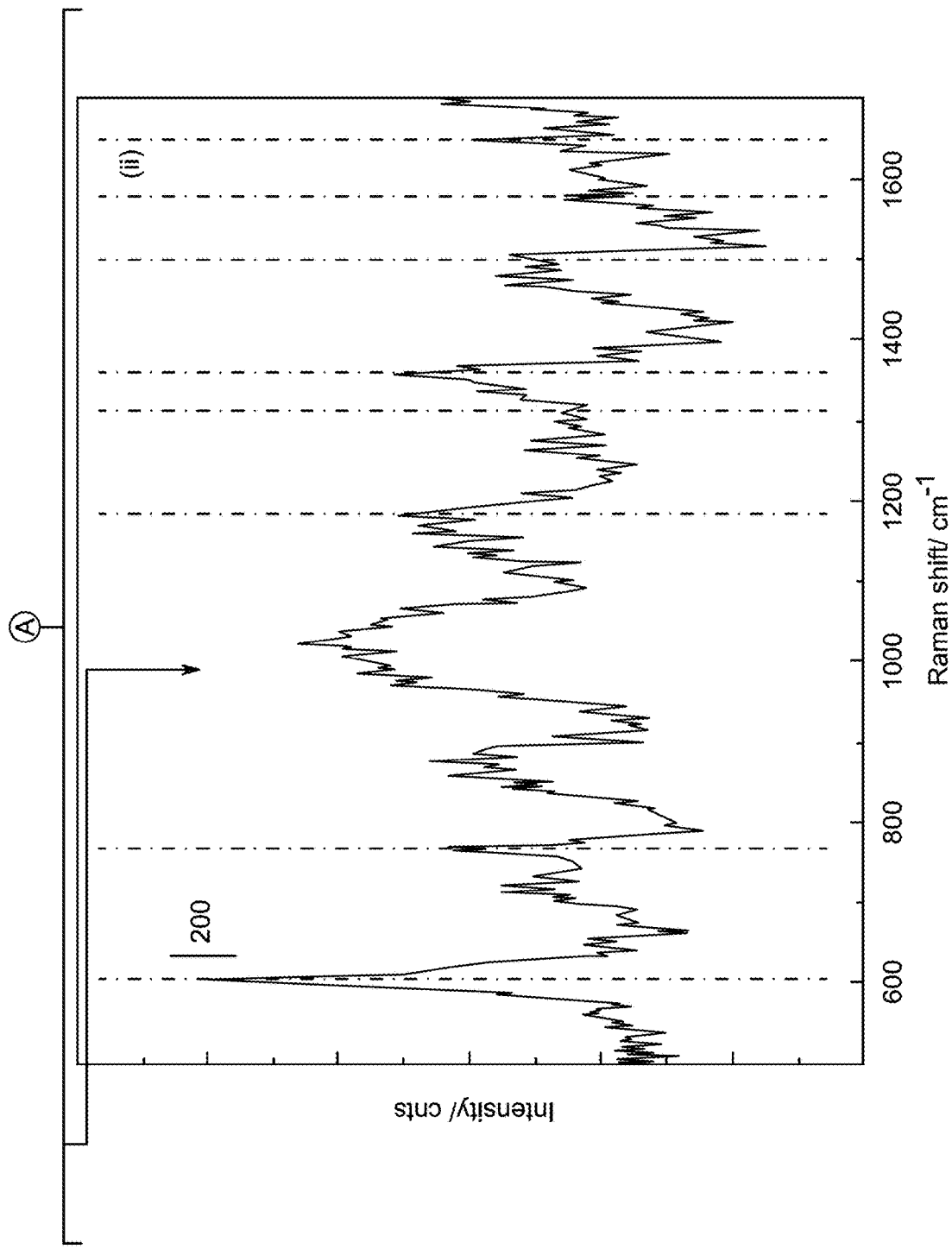
Figure 4B:
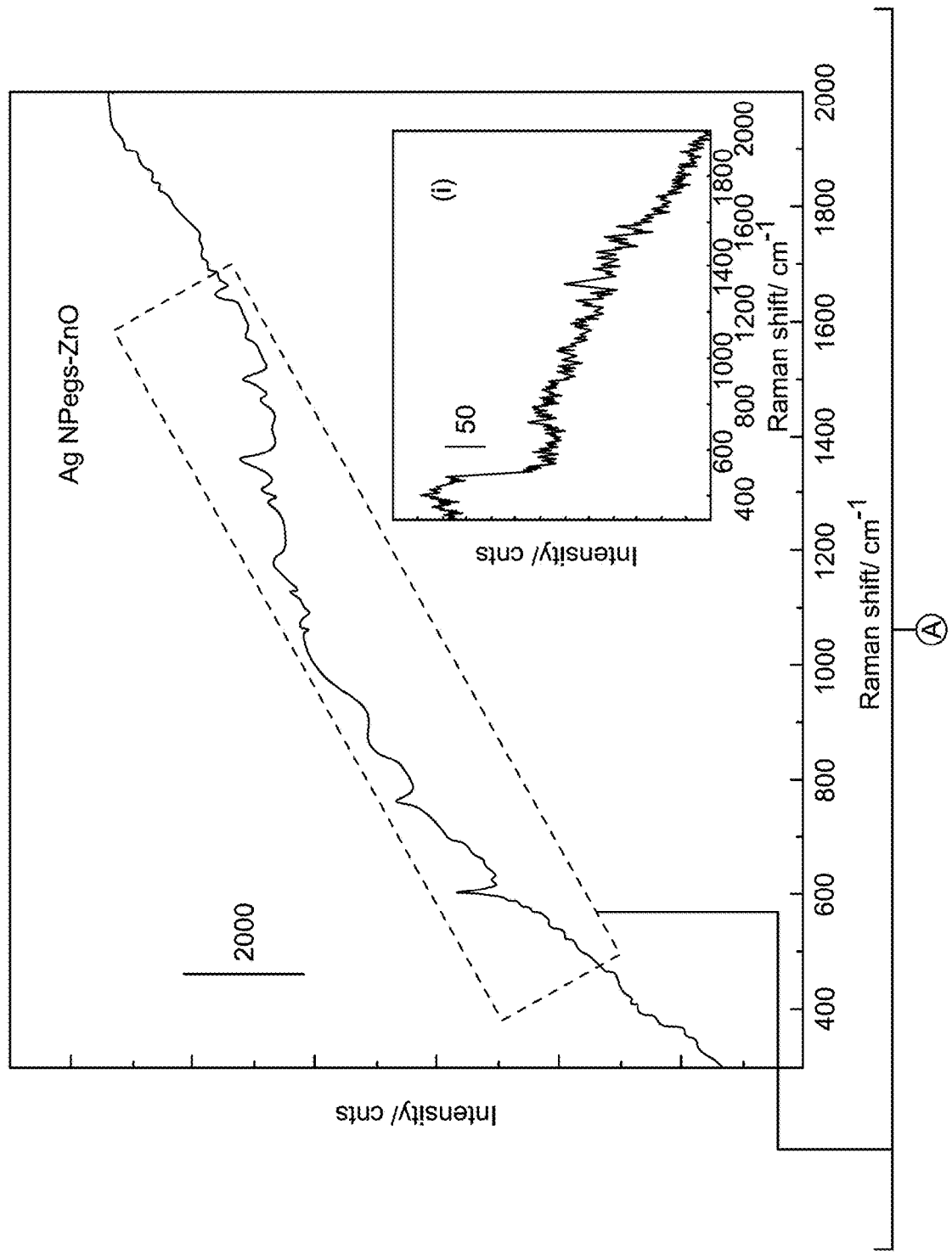
FIG. 4B illustrates SERS spectrum of R6G adsorbed on Ag NNs-ZnO, according to certain embodiments. (i): Raman spectrum of Ag NNs-ZnO without R6G (ii): Fluorescence background-subtracted SERS spectrum of R6G adsorbed on Ag NNs-ZnO along with eight bands marked by vertical dash-dotted lines.
Figure 4B:
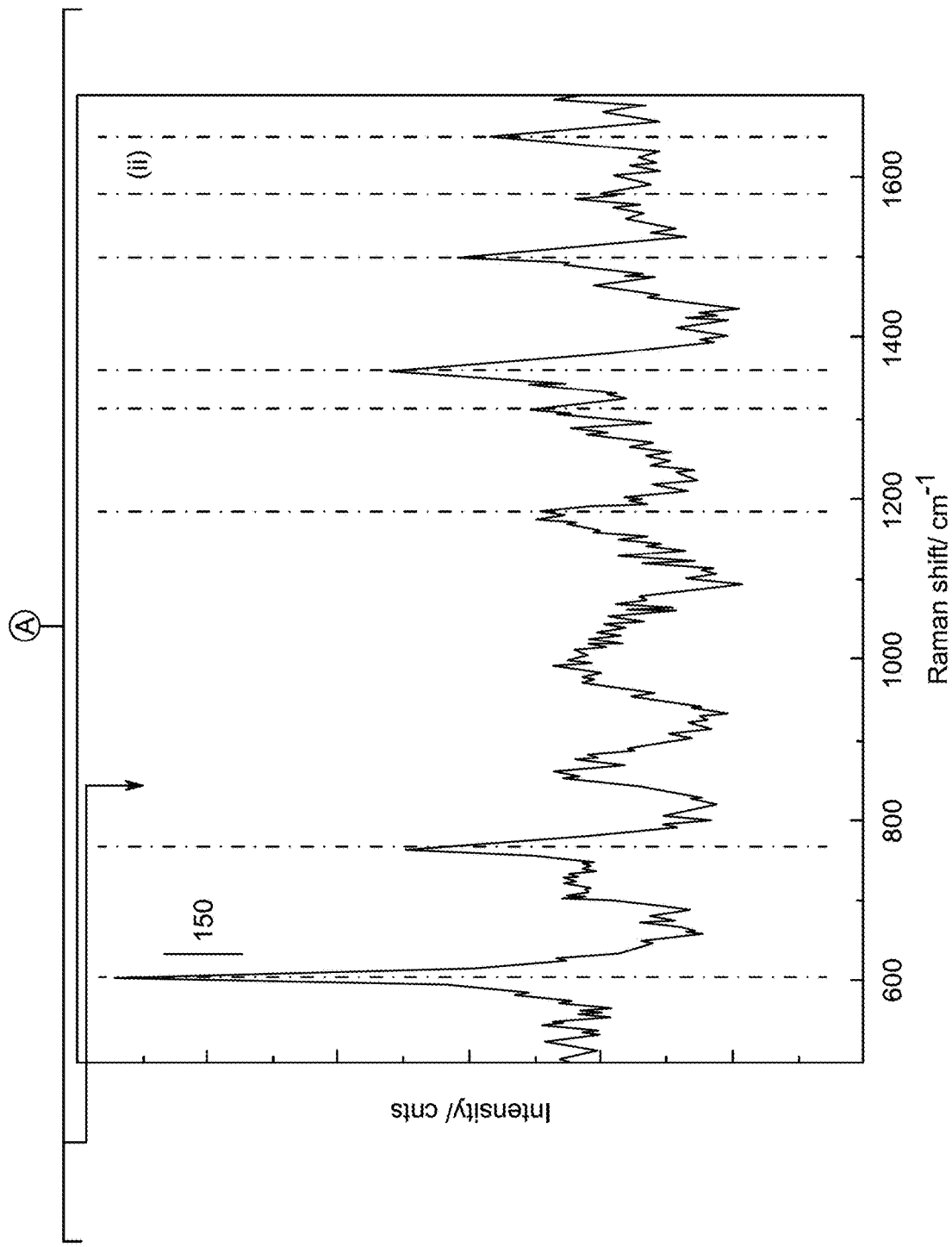
Figure 4C:
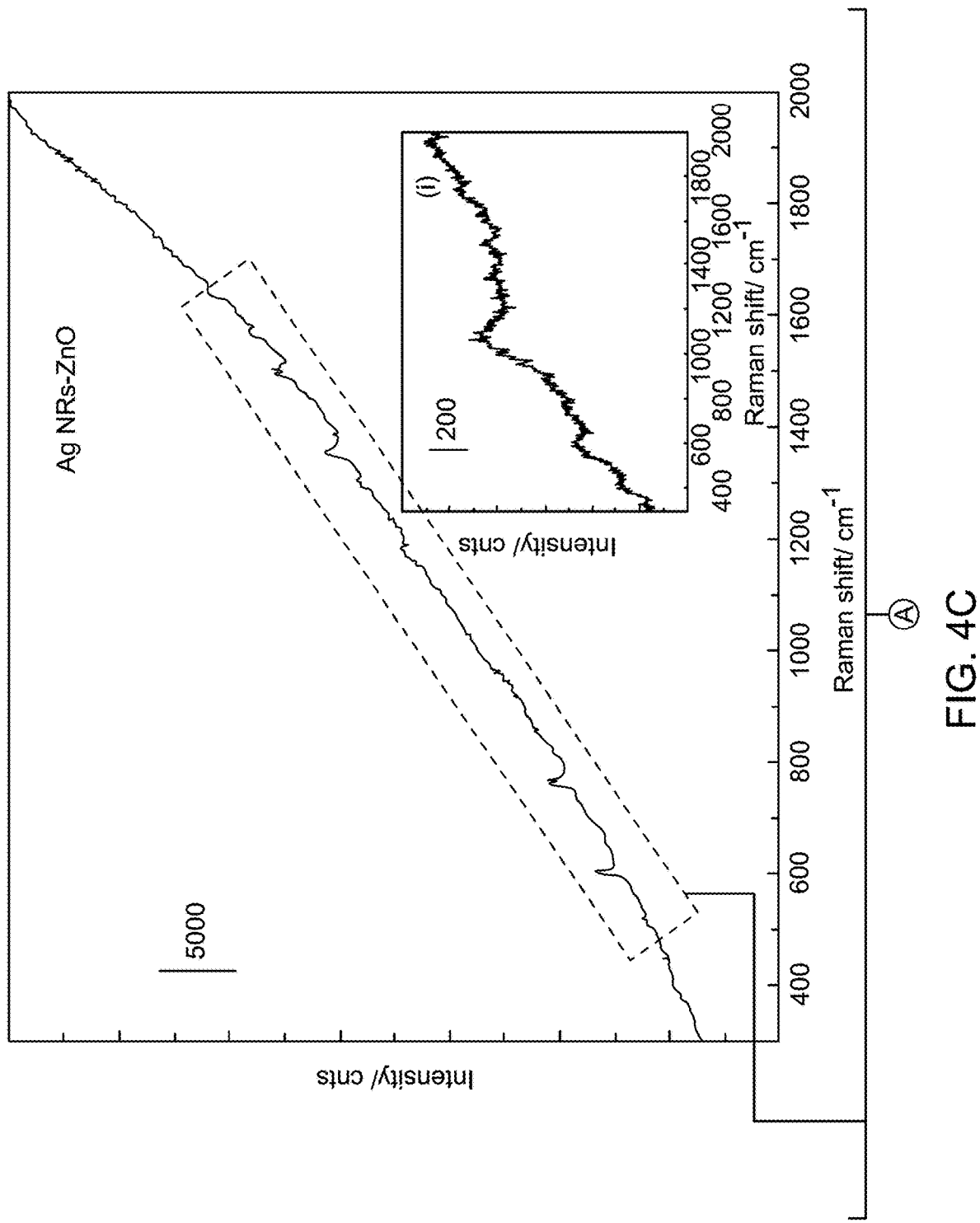
FIG. 4C illustrates SERS spectrum of R6G adsorbed on Ag NRs-ZnO, according to certain embodiments. (i): Raman spectrum of Ag NRs-ZnO without R6G (ii): Fluorescence background-subtracted SERS spectrum of R6G adsorbed on Ag NRs-ZnO along with eight bands marked by vertical dash-dotted lines.
Figure 4C:
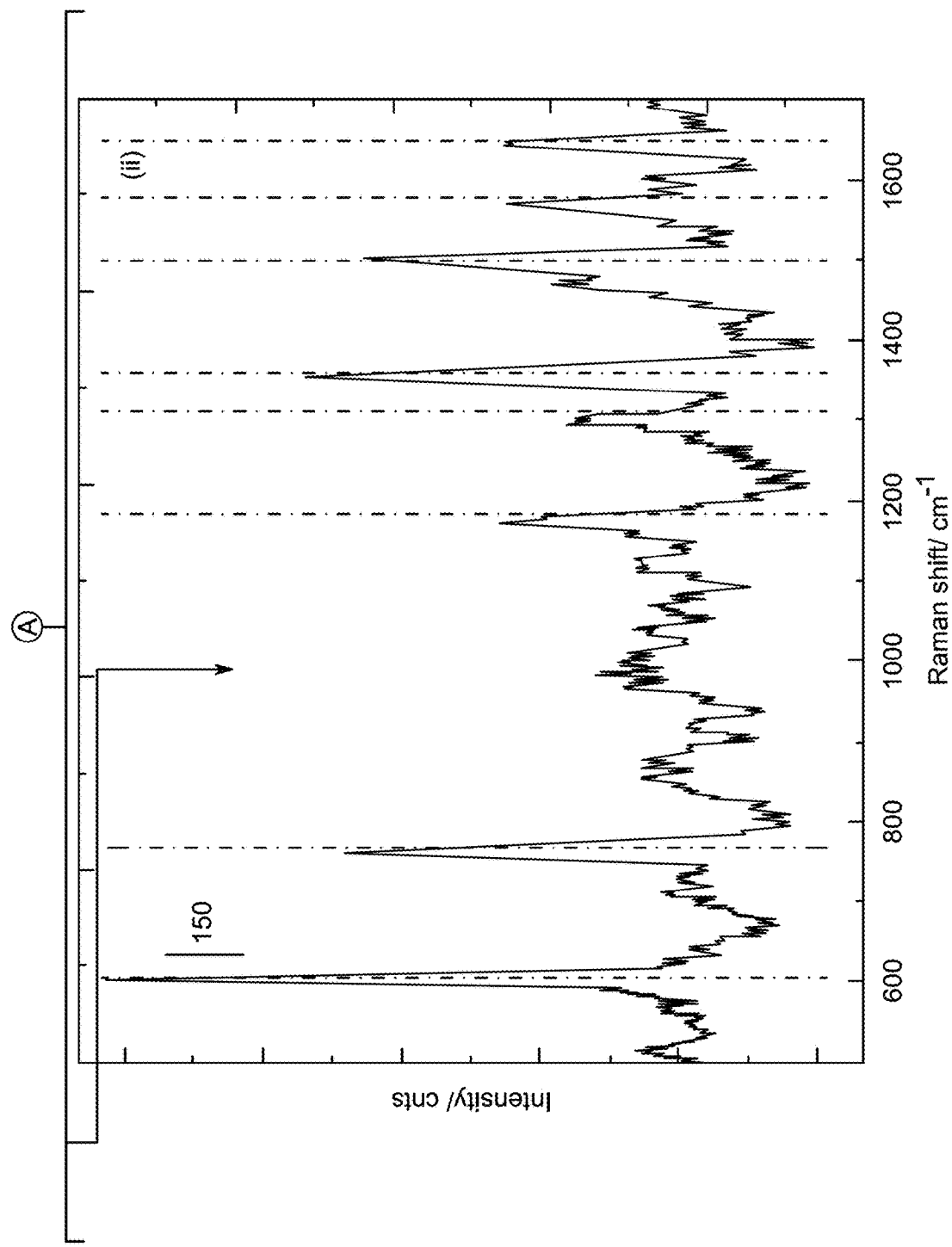

FIG. 4A shows the SERS spectrum of R6G adsorbed on Ag NPs-ZnO excited by 532 nm. SERS bands observed under this investigation are tabulated in Table 1 along with corresponding band assignments that coincided well with the reported SERS peaks of R6G. A zoom-in view of a selected area of the spectrum S1 as marked by a dashed rectangle was shown in inset (ii) of FIG. 4A. Vertical lines L1 amended in the inset (ii) of FIG. 4A guides one to point out the prominent eight SERS bands of R6G observed under this investigation. In such a case, the SERS intensity was estimated for each band and tabulated in table 1. Raman spectrum of Ag NPs-ZnO without any dyes has been recorded and shown in inset (i) of FIG. 4A. SERS spectrum S2 of R6G in presence of Ag NNs-ZnO has been shown in FIG. 4B. SERS bands observed under this investigation are tabulated in Table 1 along with corresponding band assignments that coincided well with those observed in presence of Ag NPs-ZnO and the reported SERS peaks of R6G. A zoom-in view of a selected area of the spectrum as marked by a dashed rectangle was shown in inset (ii) of FIG. 4B. Vertical lines amended in the inset (ii) of FIG. 4B guide one to point out the prominent eight SERS bands of R6G observed under this investigation. The SERS intensity was estimated for each band and tabulated in table 1. Raman spectrum of Ag NNs-ZnO without any dyes has been recorded and shown in inset (i) of FIG. 4B. As for Ag NRs-ZnO, the SERS spectrum S3 of R6G absorbed thereon has been displayed in FIG. 4C. SERS bands observed in presence of Ag NNs-ZnO were tabulated in Table 1 along with corresponding band assignments. It is noteworthy to mention that the SERS peaks coincided well with those observed in presence of Ag NPs-ZnO and Ag NNs-ZnO. A zoom-in view of a selected area of the spectrum as marked by a dashed rectangle was shown in inset (ii) of FIG. 4C. Vertical lines amended in the inset (ii) of FIG. 4C were to guide one to follow eight SERS bands of R6G found in presence of Ag NNs-ZnO. The SERS intensity was estimated for each band and tabulated in Table 1. Raman spectrum of Ag NNs-ZnO without any dyes have been recorded and shown in inset (i) of FIG. 4C. It was observed that the SERS band intensities of R6G in presence of Ag NRs-ZnO were found to be stronger compared to those observed in presence of Ag NPs-ZnO and Ag NNs-ZnO. On the other side, although the coverage density of Ag NPs-ZnO was estimated several orders higher compared to that of Ag NNs-ZnO and Ag NRs-ZnO, the SERS band intensities were found the lowest in presence of Ag NPs-ZnO. As shown in Table 1, all the eight SERS bands of R6G in presence of Ag NNs-ZnO were found to have stronger band intensities. As mentioned earlier, the EM enhancement mechanism is the dominating factor in SERS enhancement, and hence, it was speculated that EM near-field distribution might be higher in the case of Ag NNs-ZnO with reference to those that occurred in Ag NPs-ZnO and Ag NRs-ZnO. Extensive simulations have been carried out to extract EM near-field distributions for NPs-ZnO, Ag NRs-ZnO, and Ag NNs-ZnO as mentioned in the following section.

TABLE 1

SERS bands of R6G, corresponding band assignments and estimated SERS band intensities in presence of Ag NPs—ZnO, Ag NRs—ZnO and Ag NNs—ZnO.

| SERS Band of R6G (cm$^{-1}$) | Band Assignment (2, 5) | Band Intensity @Ag NPs—ZnO | Band Intensity @Ag NPegs—ZnO | Band Intensity @Ag NRs—ZnO |
|---|---|---|---|---|
| 610 | C—C ring bending mode (in-plane) in phenyl rings | Weak (645 cnts) | Moderate (944 cnts) | Strong (1262 cnts) |
| 769 | C—H bending mode (out-of-plane) | Weak (222 cnts) | Moderate (351 cnts) | Strong (773 cnts) |
| 1182 | C—H bending mode (in-plane) in xanthene ring | Weak (279 cnts) | Moderate (330 cnts) | Strong (405 cnts) |
| 1310 | Hybrid mode in xanthene/phenyl rings and NHC$_2$H$_5$ group | Weak (27 cnts) | Moderate (163 cnts) | Strong (321 cnts) |
| 1361 | C—C stretching mode in xanthene ring | Weak (283 cnts) | Moderate (438 cnts) | Strong (1063 cnts) |
| 1508 | C—C stretching mode in xanthene ring | Weak (102 cnts) | Moderate (387 cnts) | Strong (761 cnts) |
| 1579 | C—C stretching mode in phenyl ring | Weak (122 cnts) | Moderate (123 cnts) | Strong (439 cnts) |
| 1652 | C—C stretching mode in xanthene ring | Weak (178 cnts) | Moderate (320 cnts) | Strong (502 cnts) |

FDTD Simulation

In the SERS study, understanding EM near-field distributions is inevitable. According to FESEM micrographs related to Ag NPs-ZnO, Ag NRs-ZnO to Ag NNs-ZnO studied under this investigation, three sets of models were simulated to elucidate EM near-field distributions by Planc FDTD (ver. 6.2). In the first set, Ag NP of 50 nm diameter was modeled, and EM near-field distributions in each case were demonstrated for s-, p- and 45° of incident polarizations. In the second set, the Ag NRs model geometries were designed in such a way that it resembles those observed by FESEM. In the third set, Ag NNs model geometry following the approximate dimensions obtained from FESEM investigations was used in FDTD simulation. To correlate EM near-field distribution, 532 nm excitation that is normal to the model geometries was chosen in FDTD simulation so the experimental results can be validated. It is noteworthy that for the sake of simplicity, nanoobjects were considered smooth and organized in a periodic fashion, although the constituent clusters were different from each other, particularly in size and shape, as observed in FESEM investigations.

Although the charge transfer (CT) mechanism is unavoidable in SERS enhancement, the EM mechanism is known to be several orders higher, particularly for metal-based plasmonic SERS-active substrate. Twofold EM enhancement as proposed by Pitinger et al., is the underlying mechanism of EM enhancement in the SERS process. In the first process, as formulated in equation (1), EM near-field contributes to enhancing Raman scattering of the analyte and simultaneously, the second process starts by enhancing scattered Raman light from the adsorbed analytes. The details can be found elsewhere and the references therein. Therefore, the enhancement factor, M, for SERS is denoted by $$M = \left|\frac{E_L(\lambda_I)}{E_I(\lambda_I)}\right|^2 \times \left|\frac{E_L(\lambda_I \pm \lambda_R)}{E_I(\lambda_I \pm \lambda_R)}\right|^2 = M_1(\lambda_I) \times M_2(\lambda_I \pm \lambda_R) \quad (1)$$

where $E_I$ and $E_L$ are the incident and local electric fields respectively, $\lambda_I$ is the excitation wavelength, $+\lambda_R$ and $-\lambda_R$ are the wavelengths of the anti-Stokes and Stokes Raman shifts, respectively, an $M_1$ and $M_2$ are the first and second enhancement factors, respectively.

Figure 5A:
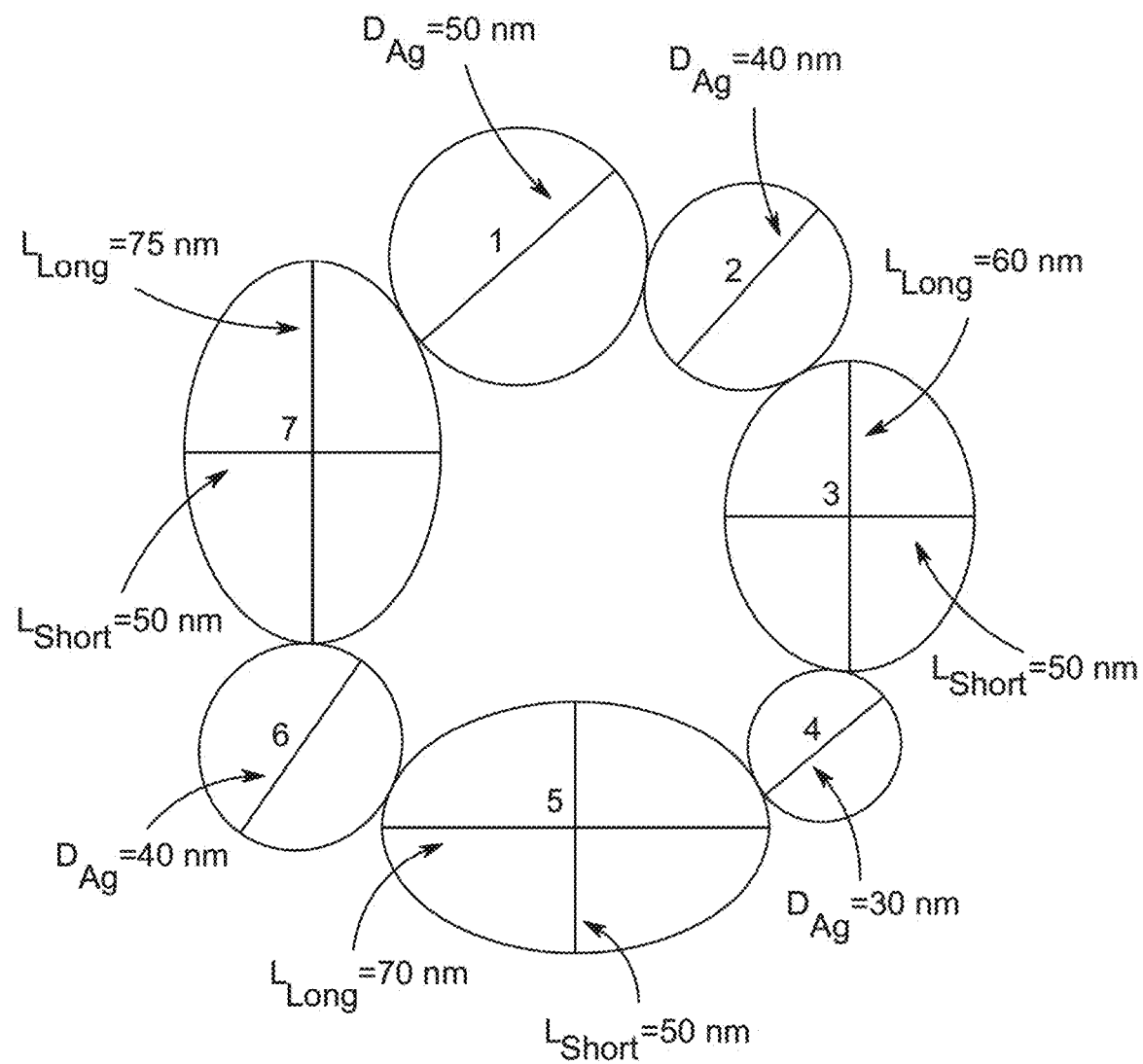
FIG. 5A illustrates a typical Ag NR model geometry consisted of nanoparticles of different shapes and sizes.

As mentioned earlier, EM near-field distribution is the main ingredient in SERS enhancement and therefore FDTD analysis was carried out in this context for typical models as shown in FIG. 5A and FIG. 6. Based on a detailed investigation on morphology as stated above in FIG. 1A-FIG. 1E, FIG. 2A-FIG. 2E, and FIG. 3A-FIG. 3C, three typical models resembling Ag NPs-ZnO, Ag NRs-ZnO, and Ag NNs-ZnO were developed as mentioned in the experimental section.

Figure 5B:
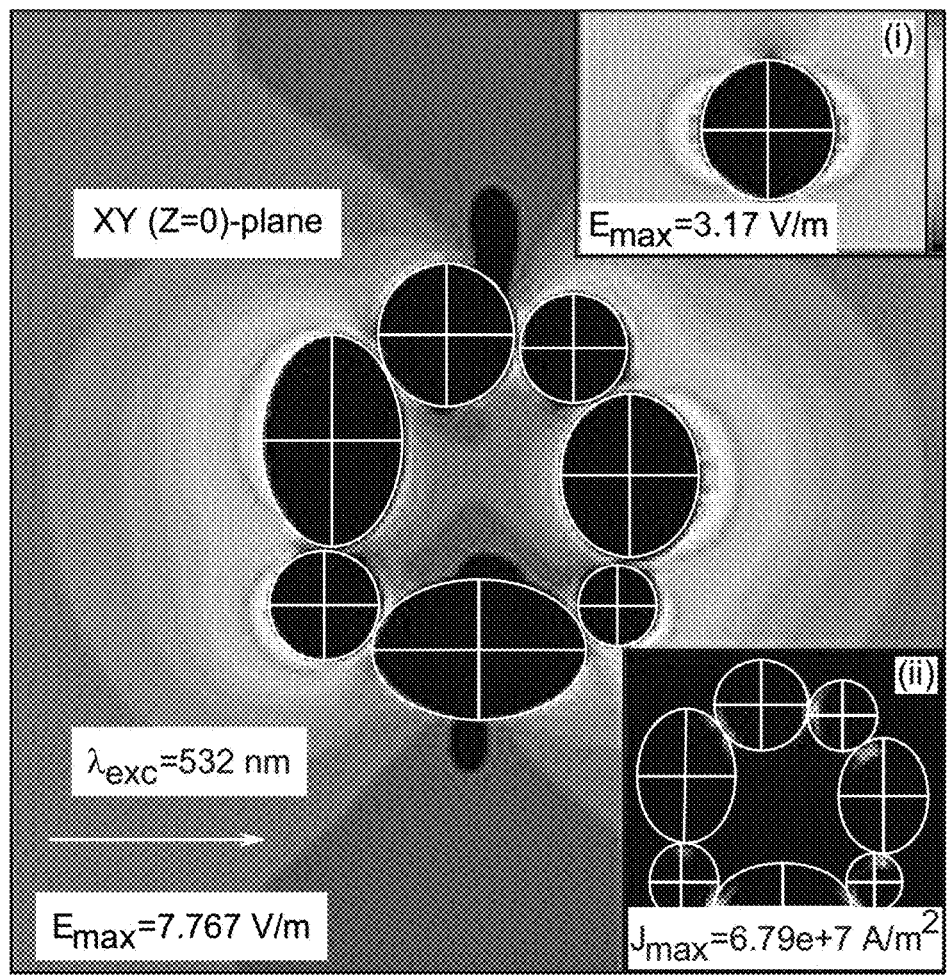
FIG. 5B illustrates EM near-field distributions of the Ag NR of FIG. 5A at XY (Z=0) plane for s- of incident polarizations. (i): EM near-field distribution of an Ag NPs (DAg=50 nm) and (ii) charge density distribution of the same model. White arrows in each figure represent polarization directions of incident excitation. Color bars represent the respective intensities observed under the simulations.
Figure 5C:
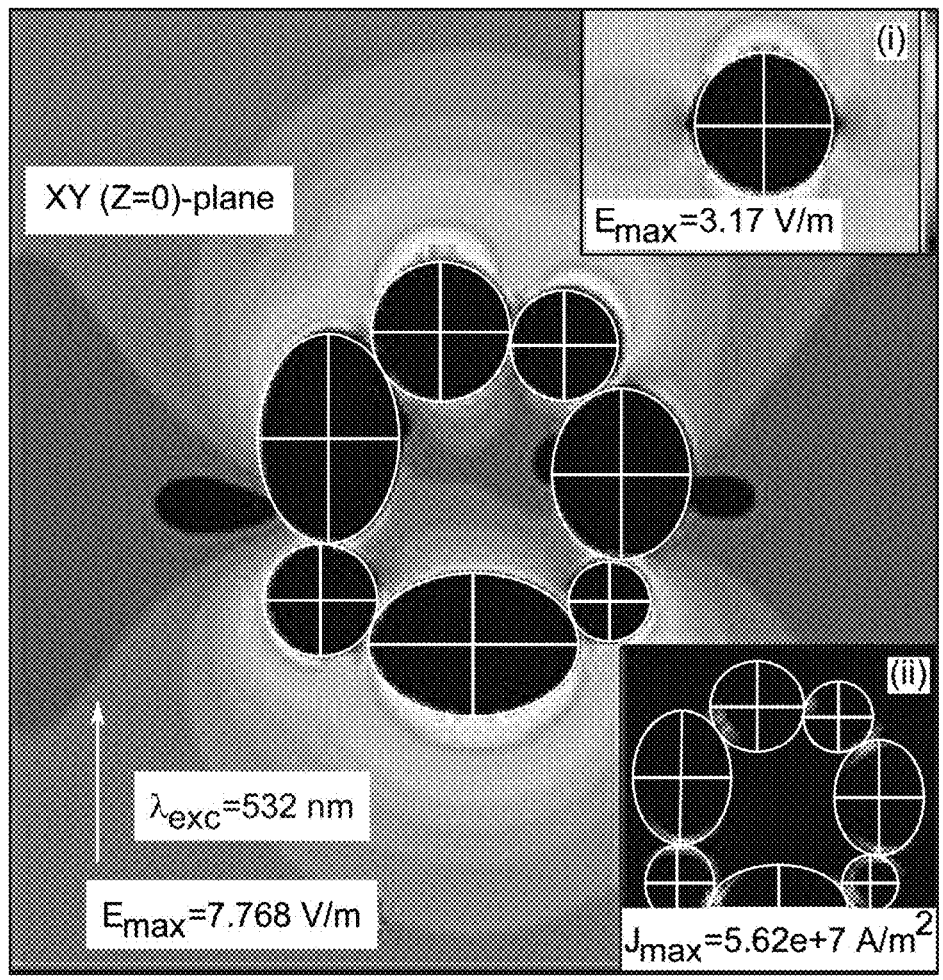
FIG. 5C illustrates EM near-field distributions of the Ag NR of FIG. 5A at XY (Z=0) plane for p- of incident polarizations. (i): EM near-field distribution of an Ag NPs (DAg=50 nm) and (ii) charge density distribution of the same model. White arrows in each figure represent polarization directions of incident excitation. Color bars represent the respective intensities observed under the simulations.
Figure 5D:
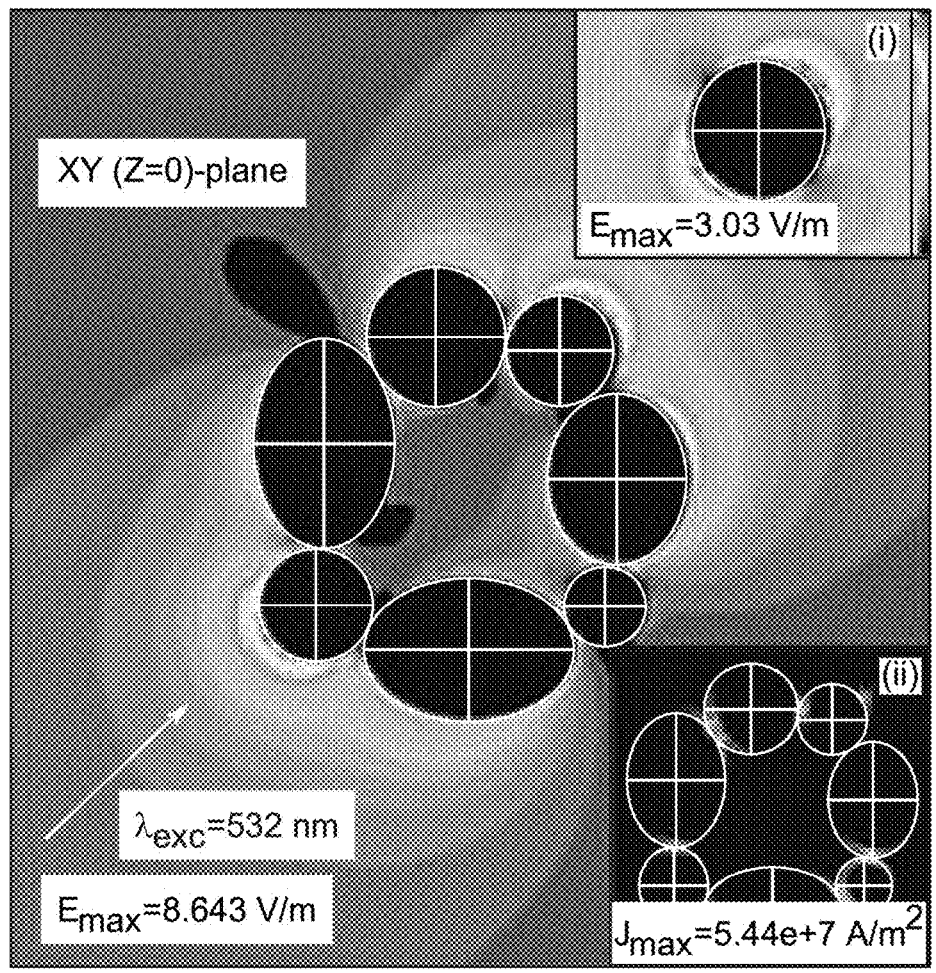
FIG. 5D illustrates EM near-field distributions of the Ag NR of FIG. 5A at XY (Z=0) plane for 45° of incident polarizations. (i): EM near-field distribution of an Ag NPs (DAg=50 nm) and (ii) charge density distribution of the same model. White arrows in each figure represent polarization directions of incident excitation. Color bars represent the respective intensities observed under the simulations.

It is well-understood that the localized EM near-field highly relies on the nanostructure. A small variation in nanoscale topography affects EM near-field distributions as well as LSPR excitation. As elaborated in FIG. 3A-FIG. 3C, the Ag NRs-ZnO used under this investigation were found to consist of Ag nanoclusters of different sizes and shapes. Therefore, it is fair to develop such an Ag NR model that resembles well to the Ag NRs-ZnO. FIG. 5A display such a model that consists of 7 nanoparticles of different sizes and shapes. Nanoparticles marked as 1, 2, 4 and 6 were spherical in shape with diameters of 50, 40, 30 and 40 nm, respectively, whereas the nanoparticles marked as 3, 5 and 7 were elliptical in shapes with long axes and short axes of 60 and 50 nm, 70 and 50 nm and 75 and 50 nm respectively. All the nanoparticles were in touch without any gap as observed and demonstrated in FIG. 3A-FIG. 3C. FIG. 5B represents EM near-field distributions at XY (Z=0) plane for the model geometry as shown in FIG. 5A and excited with incident excitation of s-polarization. The nanoparticles marked as 2, 3, 4, 6 and 7 exhibit strong EM near-field distributions with a maximum intensity of 7.767 V/m. Inset (i) of FIG. 5B shows EM near-field distribution of Ag NPs of 50 nm diameter with a maximum intensity of 3.17 V/m which is less than half of that observed in Ag NRs. It is noteworthy to mention that strong charge density was observed at the interstitials of constituent NPs of Ag NRs with a maximum intensity of 6.79×10$^7$ A/m$^2$. In the case of p-polarization, as shown in FIG. 5C, EM near-field distribution was found strong around the nanoparticles marked as 1, 2, 4, 5, 6 and 7 with a maximum intensity of 7.768 V/m. EM near-field distribution of Ag NPs of 50 nm diameter with a maximum intensity of 3.17 V/m was shown in the inset of FIG. 5C. Localized charge densities were observed at the interstitials of constituent NPs of Ag NRs as shown in inset (ii) of FIG. 5C. In the case 45° of incident polarizations, similar EM near-field distributions were observed as shown in FIG. 5D. The nanoparticles marked as 1, 2, 3, 5, and 6 exhibit strong EM near-field distributions with a maximum intensity of 8.643 V/m. Inset (i) of FIG. 5D shows EM near-field distribution of Ag NPs of 50 nm diameter with a maximum intensity of 3.03 V/m whereas the charge density distribution of Ag NRs was shown in inset (ii). It is to be noted that regardless of incident polarization, EM near-field distribution of Ag NRs was found wider and intense as high as more than double compared to those observed in Ag NPs. Therefore the SERS band intensities of R6G in presence of Ag NRs-ZnO were supposed to be enhanced compared to those obtained in presence of Ag NPs-ZnO. Indeed as shown in FIG. 4A-FIG. 4C and Table 1, the SERS band intensities of R6G in presence of Ag NRs-ZnO were found more than double compared to those obtained in presence of Ag NPs-ZnO. This reminds once again the superiority of 2D SERS-active substrate (Ag NRs-ZnO) over the 0D SERS-active substrate (Ag NPs-ZnO).

Figure 6A:
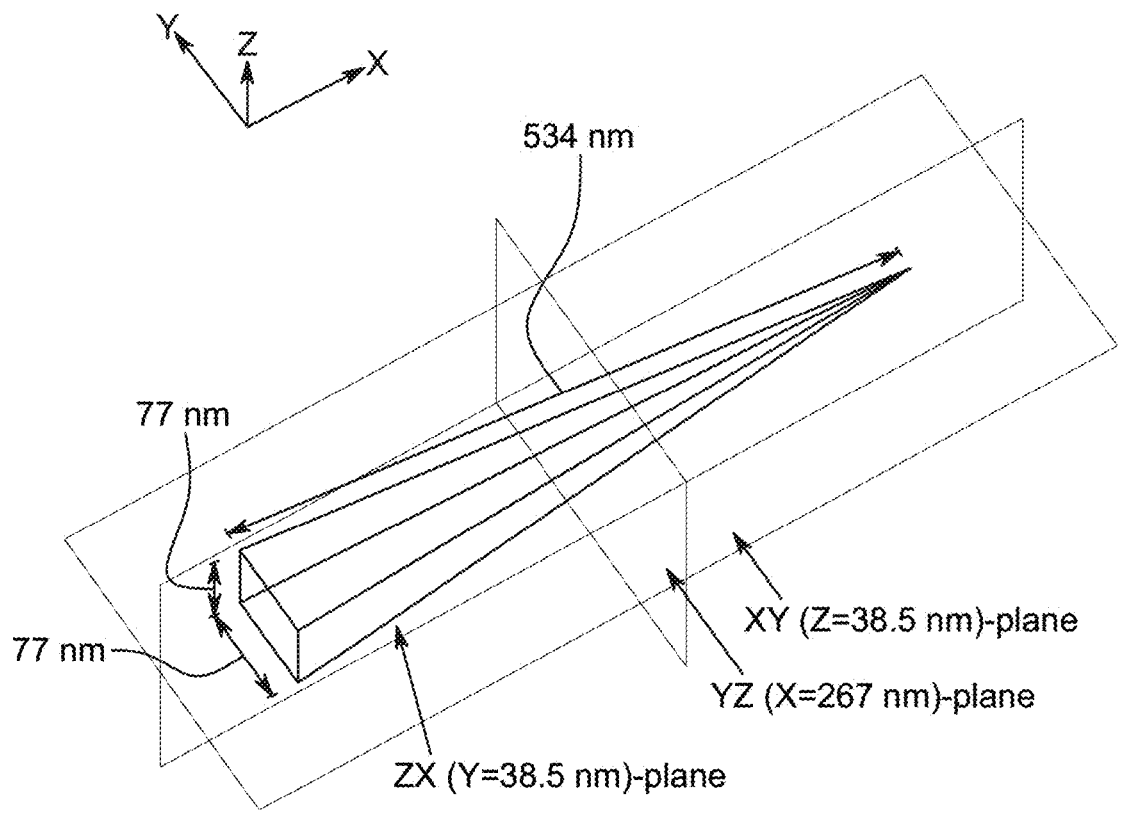
FIG. 6A illustrates a typical Ag NNs model used in FDTD simulation, according to certain embodiments, and specific planes of interest XY (Z=38.5 nm), YZ (X=267 nm) and ZX (Y=38.5 nm).
Figure 6B:
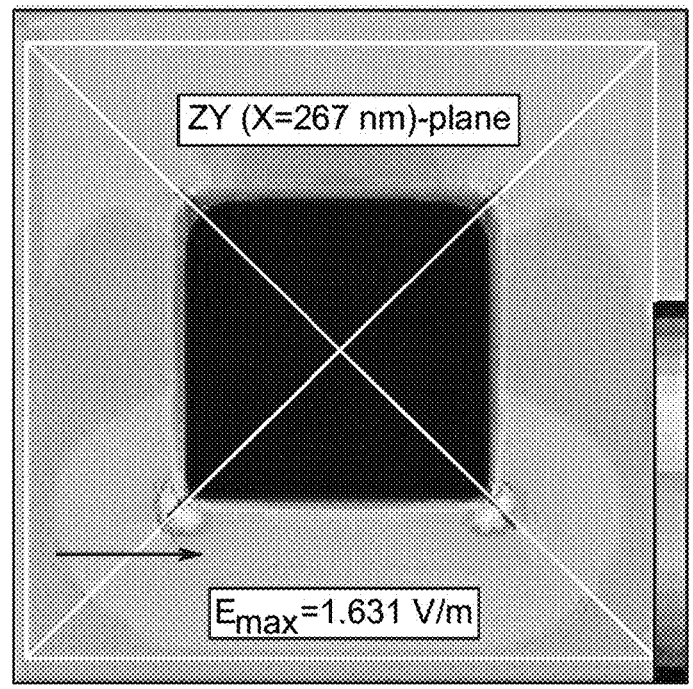
FIG. 6B illustrates EM near-field distributions extracted for s-polarization and at YZ (X=267 nm)-plane of the FDTD simulation of FIG. 6A. Arrows in each figure represent polarization directions of incident excitation. Color bars represent the respective intensities observed under the simulations.
Figure 6C:
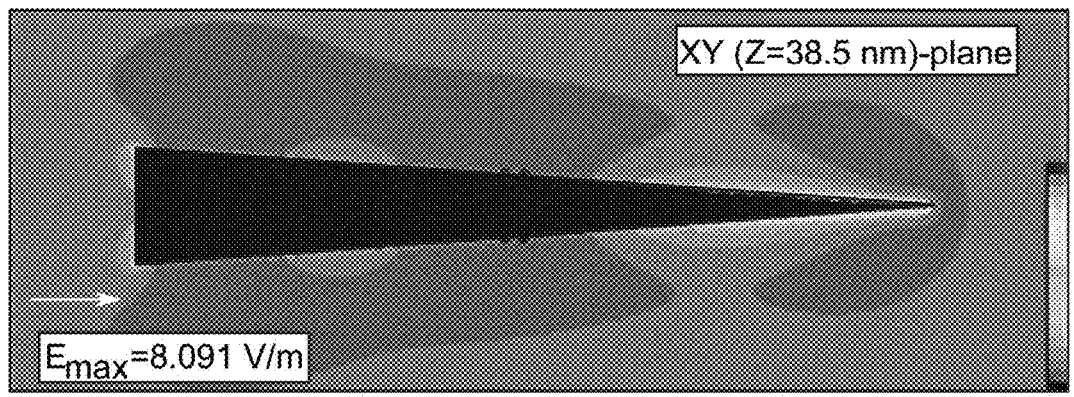
FIG. 6C illustrates EM near-field distributions extracted for s-polarization and at XY (Z=38.5 nm)-plane of the FDTD simulation of FIG. 6A. Arrows in each figure represent polarization directions of incident excitation. Color bars represent the respective intensities observed under the simulations.
Figure 6D:
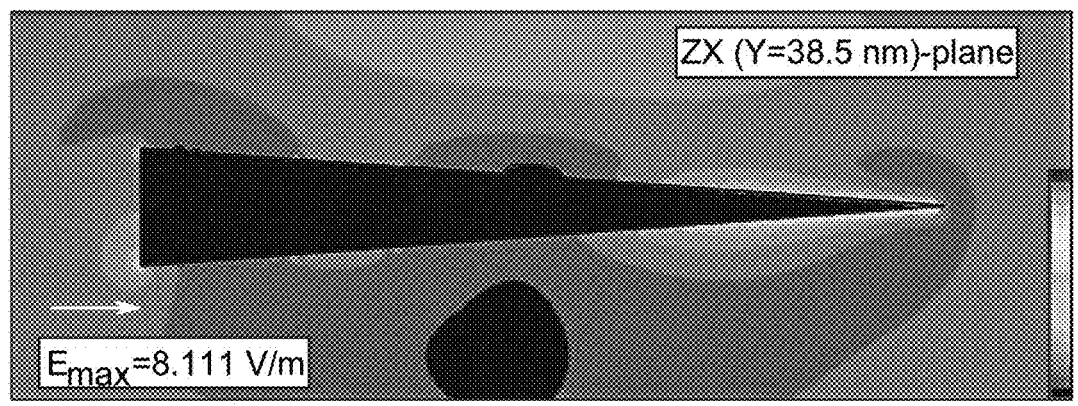
FIG. 6D illustrates EM near-field distributions extracted for s-polarization and at ZX (Y=38.5 nm)-plane of the FDTD simulation of FIG. 6A. Arrows in each figure represent polarization directions of incident excitation. Color bars represent the respective intensities observed under the simulations.
Figure 6E:
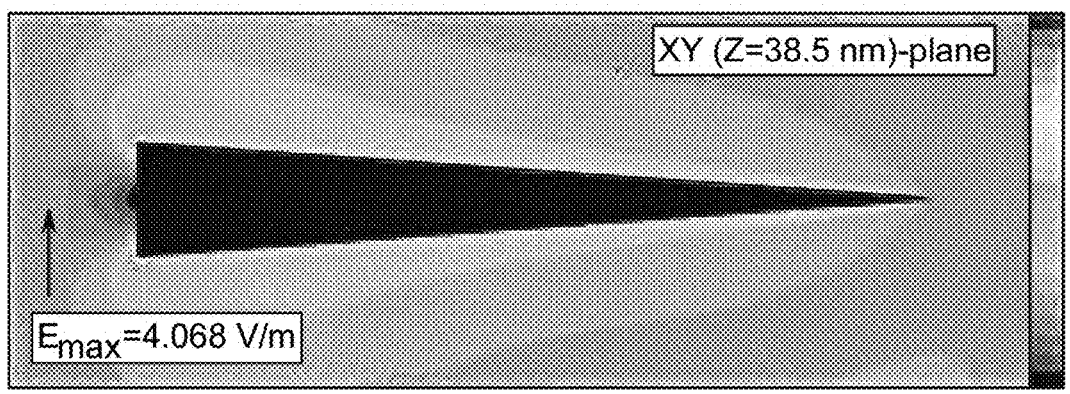
FIG. 6E illustrates EM near-field distributions extracted for p-polarization and at XY (Z=38.5 nm)-plane of the FDTD simulation of FIG. 6A. Arrows in each figure represent polarization directions of incident excitation. Color bars represent the respective intensities observed under the simulations.
Figure 6F:
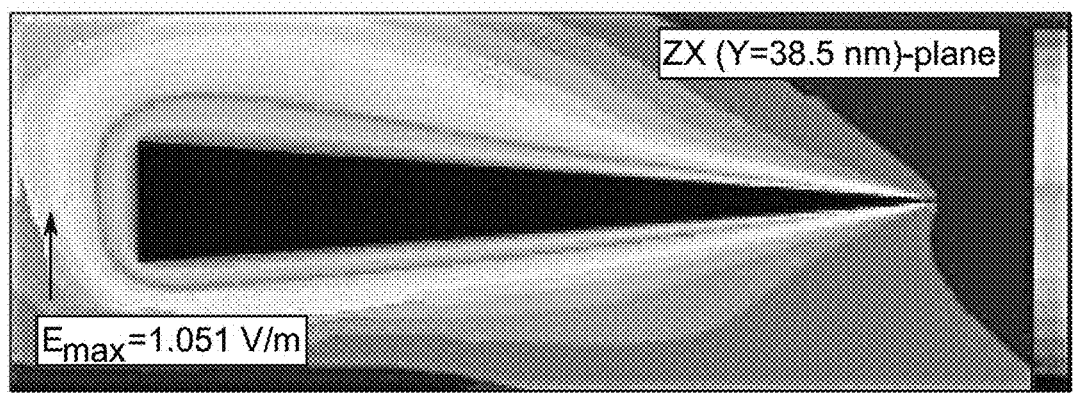
FIG. 6F illustrates EM near-field distributions extracted for p-polarization and at ZX (Y=38.5 nm)-plane of the FDTD simulation of FIG. 6A. Arrows in each figure represent polarization directions of incident excitation. Color bars represent the respective intensities observed under the simulations.
Figure 6G:
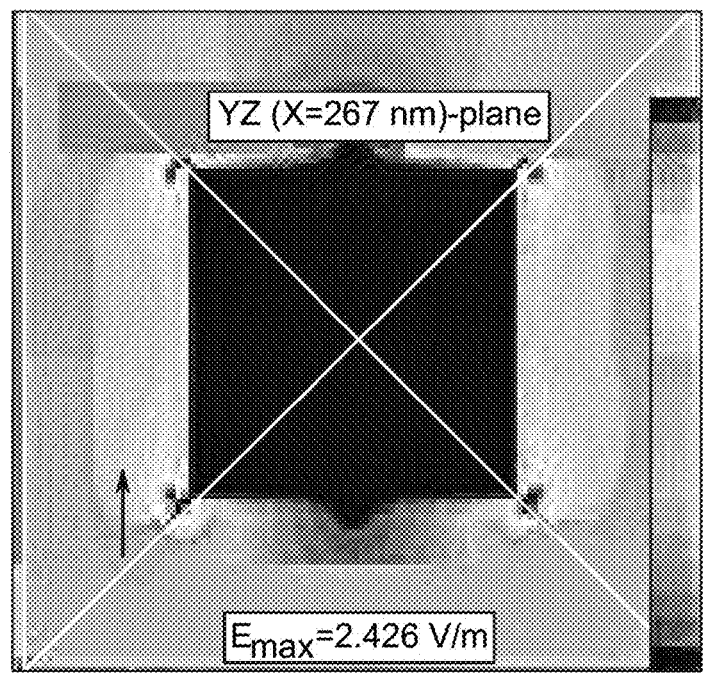
FIG. 6G illustrates EM near-field distributions extracted for p-polarization and at YZ (X=267 nm)-plane of the FDTD simulation of FIG. 6A. Arrows in each figure represent polarization directions of incident excitation. Color bars represent the respective intensities observed under the simulations.

A 1D nanostructure, such as nanorod or nanowire shows a "lightening rod effect" implying the fact that EM near-field distributions get localized at the two ends provided that incident polarization coincides along the long axis and the dimension of 1D nanorod match well to the excitation. The intensity and distribution of such localized EM near-fields determine the SERS enhancement of the target analyte. The Ag NNs-ZnO studied under this investigation indeed showed strong SERS enhancement of R6G as shown and elaborated in FIG. 4A-FIG. 4C and Table 1. In this context, an FDTD model geometry was developed and the dimensions (Length 534 nm and Base 77 nm) were chosen in such a way so that the model resembles as close as possible to that as observed by FESEM investigations and shown in FIG. 2A-FIG. 2E. FIG. 6A represents the Ag NNs model along with dimensions and three planes of interest. The XY (Z=38.5 nm)-plane is normal to the excitation and across the center of Ag NNs. The ZX (Y=38.5 nm)-plane is parallel to the excitation and across the center of Ag NNs, whereas the YZ (X=267 nm) is parallel to the excitation but across the middle of Ag NNs as shown in FIG. 6A. EM near-field distributions were extracted for the above-mentioned three planes at s-, p- and 45° of incident polarizations. FIG. 6B-FIG. 6D show EM near-field distributions of Ag NNs extracted for s-polarization and at the planes of YZ (X=267 nm), XY (Z=38.5 nm) and ZX (Y=38.5 nm), respectively. It was evident that strong EM near-field with the maximum intensities of 8.091 and 8.111 V/m was observed at the sharp edges for XY (Z=38.5 nm) and ZX (Y=38.5 nm) planes whereas weak EM near-field with the maximum intensity of 1.631 V/m was found at two corners for (X=267 nm)-plane. FIG. 6E-FIG. 6G displays EM near-field distributions of Ag NNs extracted for p-polarization and at the planes of XY (Z=38.5 nm), ZX (Y=38.5 nm) and YZ (X=267 nm), respectively. At XY (Z=38.5 nm)-plane, EM near-fields were found localized near the base of Ag NNs with the maximum intensity of 4.068 V/m as shown in FIG. 6E. Although the maximum intensity was nearly half of that found at s-polarization in the same plane, EM near-fields were distributed wider around the Ag NNs. It was further confirmed with the EM near-field distribution at YZ (X=267 nm)-plane as shown in FIG. 6G having moderate and wider intensity with the maximum intensity of 2.426 V/m particularly confined at the corners. However, negligible EM near-field distribution was observed at p-polarization in ZX (Y=38.5 nm)-plane as shown in FIG. 6F. In the case of 45° of incident polarization, fairly strong EM near-field confinements with the maximum intensity of 5.854 V/m and 5.646 V/m were observed at both ends in XY (Z=38.5 nm)-plane and ZX (Y-38.5 nm)-plane respectively, although wider distribution was noted around the Ag NNs in XY (Z=38.5 nm)-plane only. Moderate EM near-field confinements with the maximum intensity of 1.963 V/m were observed on all four edges of Ag NNs in the YZ (X=38.5 nm)-plane along with wider distribution.

Figure 6H:
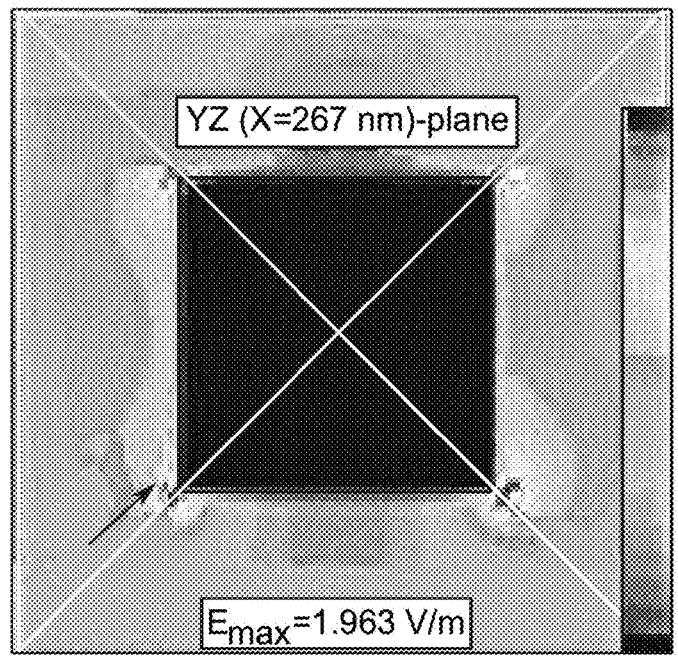
FIG. 6H illustrates EM near-field distributions extracted for 45° of incident polarization and at YZ (X=267 nm)-plane of the FDTD simulation of FIG. 6A. Arrows in each figure represent polarization directions of incident excitation. Color bars represent the respective intensities observed under the simulations.
Figure 6I:
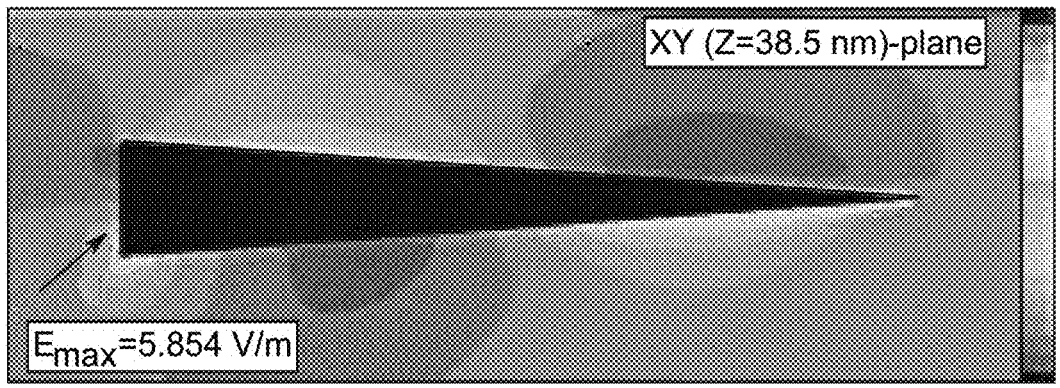
FIG. 6I illustrates EM near-field distributions extracted for 45° of incident polarization and at XY (Z=38.5 nm)-plane of the FDTD simulation of FIG. 6A. Arrows in each figure represent polarization directions of incident excitation. Color bars represent the respective intensities observed under the simulations.
Figure 6J:
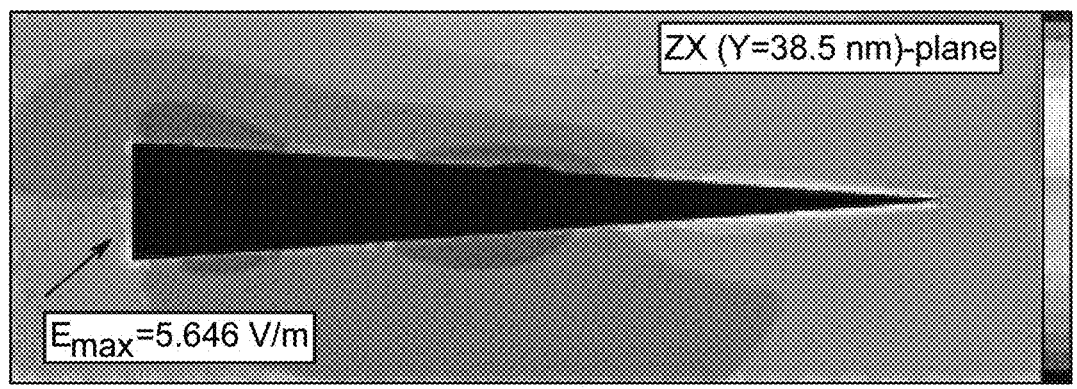
FIG. 6J illustrates EM near-field distributions extracted for 45° of incident polarization and at ZX (Y=38.5 nm)-plane of the FDTD simulation of FIG. 6A. Arrows in each figure represent polarization directions of incident excitation. Color bars represent the respective intensities observed under the simulations.
Figure 7B:
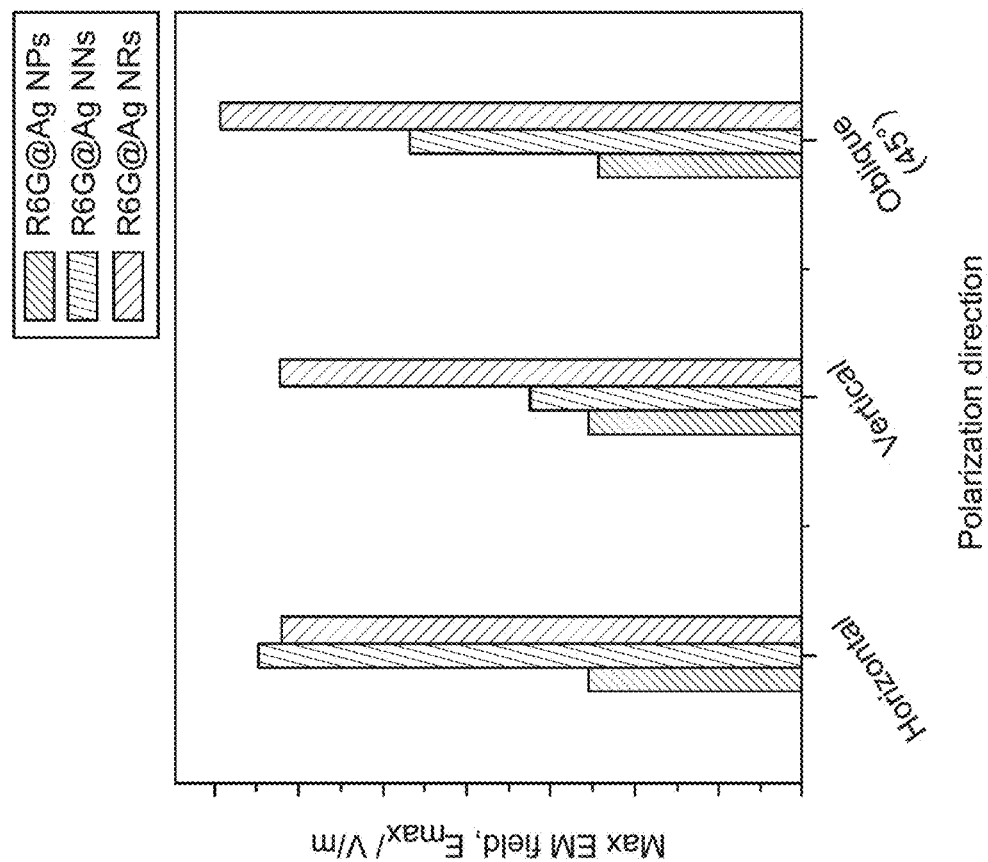
FIG. 7B illustrates maximum EM near-field intensity at s (horizontal)-, p (vertical)- and 45° (oblique) of incident polarizations for Ag NPs, Ag NNs and Ag NRs models used in FDTD simulation.
Figure 7A:
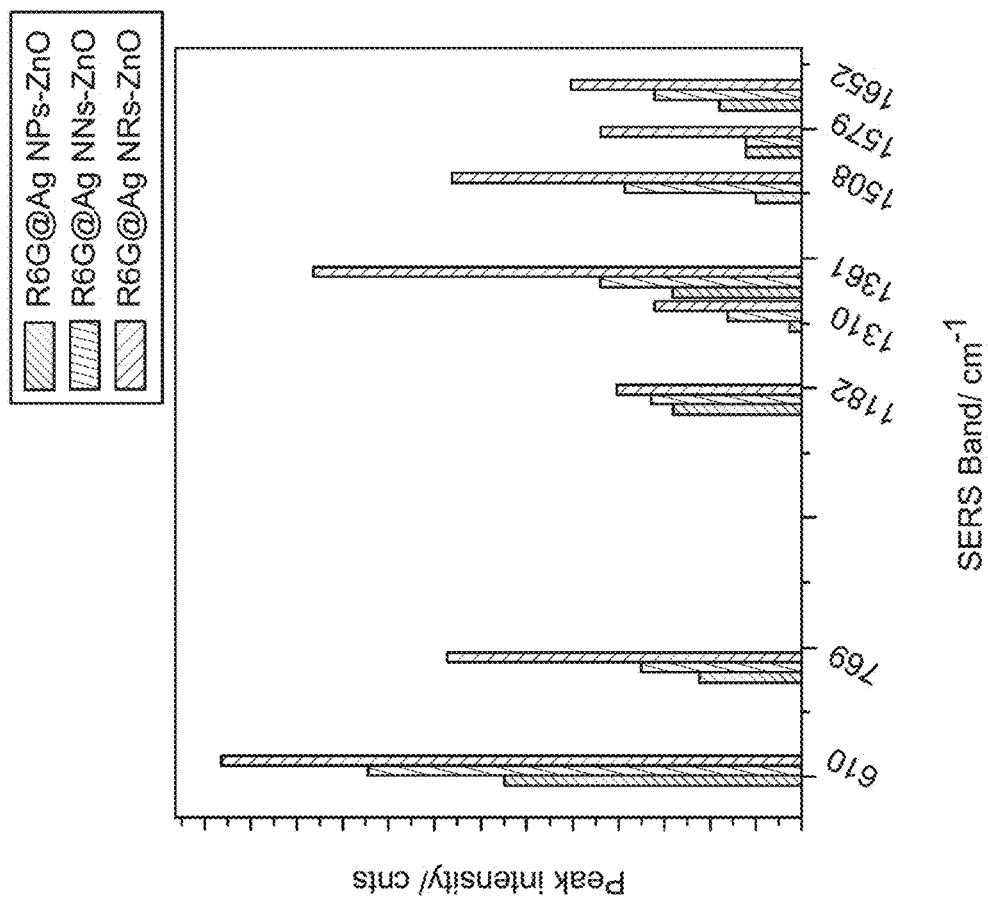
FIG. 7A illustrates eight available SERS band intensities of R6G in presence of Ag NPs-ZnO, Ag NNs-ZnO and Ag NRs-ZnO, according to certain embodiments.
Figure 7C:
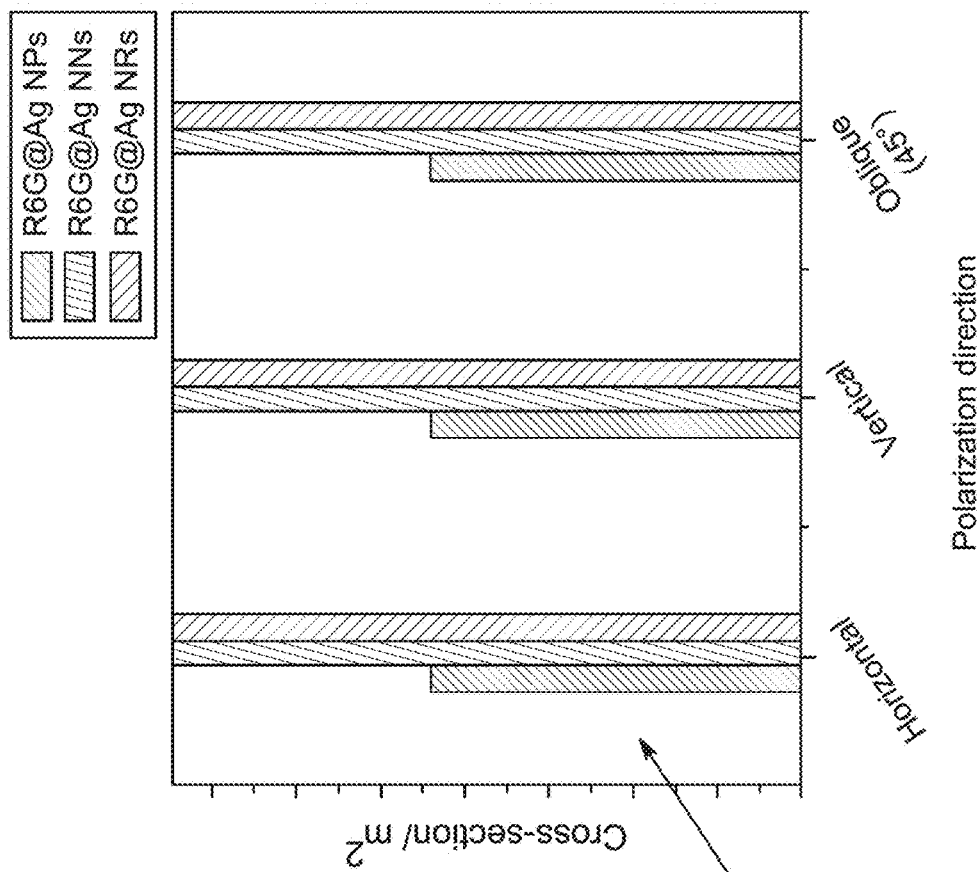
FIG. 7C shows scattering cross-sections obtained at s (horizontal)-, p (vertical)- and 45° (oblique) of incident polarizations using Ag NPs, Ag NNs and Ag NRs as nanoscatterers in FDTD simulation, according to some embodiments.
Figure 7D:
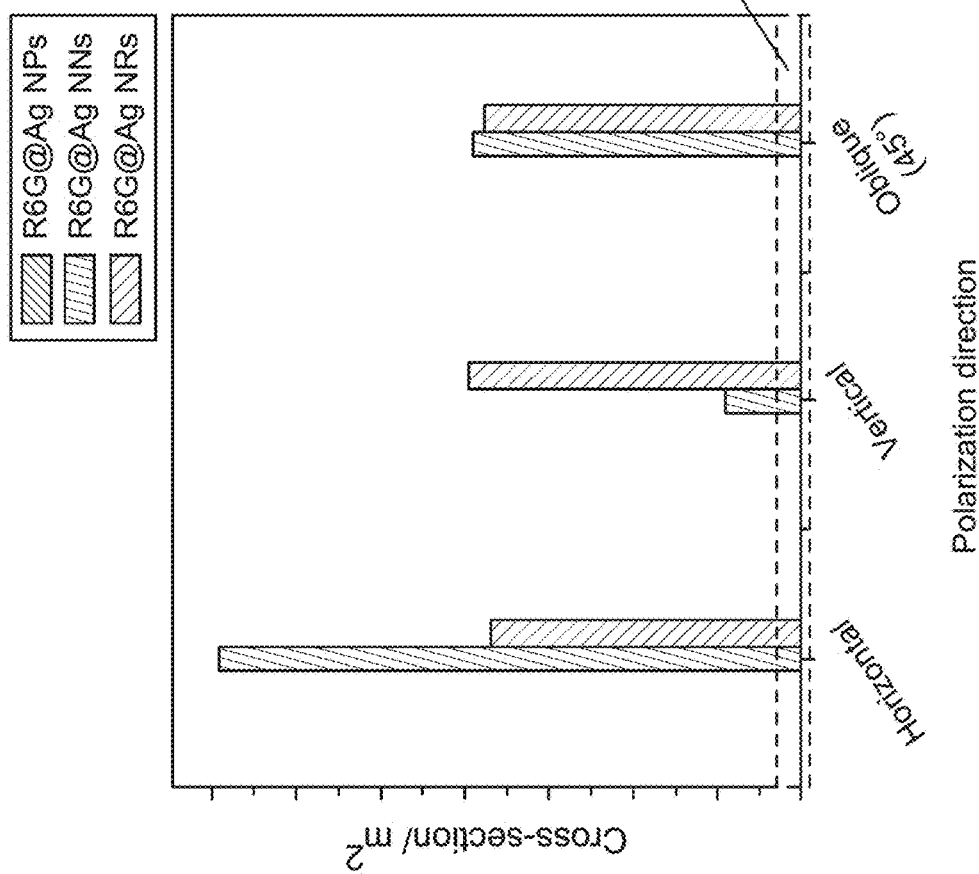
FIG. 7D shows scattering cross-sections obtained at s (horizontal)-, p (vertical)- and 45° (oblique) of incident polarizations using Ag NPs, Ag NNs and Ag NRs as nanoscatterers in FDTD simulation, according to some embodiments.

It is noteworthy to mention that EM near-field distributions were found wider around the Ag NNs in p- and 45° of incident polarizations. To the extend, sites of EM near-field confinement were found higher as shown in FIG. 6G-FIG. 6H. In such a scenario, it is expected that more analyte will be influenced by the EM near-field and thus enhanced Raman signal of the target analyte will be available. However, FDTD simulations for Ag NR model geometry revealed that more nanoparticles were having stronger and wider EM near-field distribution compared to those extracted for Ag NP and Ag NNs model geometry as shown in FIG. 5A-FIG. 5D and FIG. 6A-FIG. 6J. However, EM near-field distributions for Ag NNs model geometry were found more favorable compared to those obtained in Ag NPs model geometry as shown in FIG. 7B. Since EM near-field is the main ingredient in enhancing SERS signals of the target analyte, it was speculated that SERs bands of R6G in presence of Ag NRs-ZnO will be higher compared to those obtained in presence of Ag NNs-ZnO and Ag NPs-ZnO. Indeed as shown in FIG. 7A, eight available SERS bands of R6G as observed under this investigation were having the strongest enhanced in presence of Ag NRs-ZnO. Similar to the trend of EM near-fields, SERS bands of R6G in presence of Ag NNs-ZnO showed higher enhancement compared to those obtained in presence of Ag NPs-ZnO. Scattering cross-section indicates the amount of power scattered by the nanoscatters per solid angle over the amount of power of incident excitation. FIG. 7C-FIG. 7D show scattering cross-sections obtained at s (horizontal)-, p (vertical)- and 45° (oblique) of incident polarizations using Ag NPs, Ag NNs and Ag NRs as nanoscatterers in FDTD simulation. In the case of Ag NNs, the scattering cross-sections at s- and 45° of incident polarizations were found higher compared to those in the case of Ag NPs and Ag NRs. On the other hand, at p-polarization, Ag NNs showed uniform and higher scattering cross-section with reference to those obtained at Ag NPs and Ag NRs.

Ag NPs-ZnO, Ag NNs-ZnO and Ag NRs-ZnO have been considered to demonstrate the impact of EM near-field distributions on SERS enhancements of corresponding 0D- (i.e. Ag NPs-ZnO), 1D- (i.e. Ag NNs-ZnO) and 2D- (i.e. Ag NRs-ZnO) nanostructures. Ag NPs-ZnO, Ag NNs-ZnO and Ag NRs-ZnO fabricated on ZnO ultrathin layer through sputtering technique have been characterized thoroughly by high-resolution FESEM. FESEM micrographs confirmed a relatively narrow size distribution, 48.88±8.32 nm of Ag NPs-ZnO along with an estimated coverage density of $\sim 4 \times 10^{10}$ particles/cm$^{-2}$. In the case of 1D nanostructures, Ag NNs-ZnO were estimated to be relatively broadened length distribution, 534.36±85.61 nm and relatively narrow base distribution, 77.39±25.25 nm along with an estimated coverage density of $\sim 5 \times 10^8$ particles/cm$^{-2}$. However, as for 2D nanostructures, the FESEM micrograph revealed that Ag-NRs-ZnO were consisted of Ag clusters of various shapes and sizes, instead of a perfect ring structure along with a much lower coverage density of $\sim 8.05 \times 10^3$ particles/cm$^{-2}$. The SERS-activities of Ag-NPs-ZnO, Ag-NNs-ZnO and Ag-NRs-ZnO nanostructures were evaluated using a microscopic SERS setup and R6G as standard Raman-active dye. Ag NRs-ZnO showed higher enhancement in SERS-activity compared to those observed in presence of Ag NPs-ZnO and Ag NNs-ZnO. To demonstrate and understand the impact of EM near-fields, three models resembling the Ag NPs-ZnO, Ag NNs-ZnO and Ag-NRs-ZnO nanostructures have been analysed by FDTD simulation. EM near-field distributions at different planes and different incident polarizations have been extracted and correlated to the SERS-activities of the corresponding nanostructures. Strong and higher distribution of EM near-field in case of Ag NRs geometry supported the higher SERS-activity as observed in SERS experiments. Unlike Ag-NPs-ZnO and Ag-NNs-ZnO, it was revealed by FESEM investigations that Ag NRs-ZnO were consisted of Ag clusters of different sizes and shapes. It was speculated that Ag NRs-ZnO facilitated a higher population of SHSs and thus had higher SERS-activity.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A surface-enhanced Raman scattering-active electrode, comprising:
   a solid support;
   a porous oxide layer comprising transition metal oxide nanoparticles present on a surface of the solid support and has a mean pore size of 2 to 30 nm, wherein the transition metal oxide nanoparticles comprise nanoparticles of at least one selected from the group consisting of barium titanate, strontium titanate, lithium niobate and lanthanum calcium manganite; and
   at least one of noble metal nanoneedles and noble metal nanorings present on the porous oxide layer;
   wherein the noble metal nanoneedles have an average length of 350-800 nm, a flat end with an average width in a range of 100-150 nm, and a pointed end; and
   wherein the noble metal nanorings have a thickness of 50-300 nm and are present in the form of annular clusters having elliptical shapes with an average diameter in a range of 35-60 nm.

2. The surface-enhanced Raman scattering-active electrode of claim 1, wherein the noble metal is selected from the group consisting of gold, platinum, palladium, ruthenium, rhodium, osmium, silver, copper, mercury, rhenium, iridium, and alloys thereof.

3. The surface-enhanced Raman scattering-active electrode of claim 1, wherein the solid support is glass, the noble metal is silver, and the transition metal oxide nanoparticles have a mean particle size of 10 to 50 nm.

4. The surface-enhanced Raman scattering-active electrode of claim 1, wherein the zinc oxide nanoparticles are present in the porous oxide layer as agglomerates having a mean size of 150 to 300 nm, and a coverage density of the noble metal nanoneedles present on the porous oxide layer is $4\times10^8$-$6\times10^8$ particles/cm$^{-2}$.

5. The surface-enhanced Raman scattering-active electrode of claim 1, wherein a coverage density of the noble metal nanorings present on the zinc oxide is $7\times10^3$-$9\times10^3$ particles/cm$^{-2}$ and wherein the noble metal nanorings are present as annular clusters of 6-10 nanorings.

6. The surface-enhanced Raman scattering-active electrode of claim 1, wherein 1.2-8 times greater enhancement in a surface-enhanced Raman scattering activity is obtained when the surface-enhanced Raman scattering-active electrode comprises the noble metal nanorings in comparison to the noble metal nanoneedles.

\* \* \* \* \*